United States Patent
Berger et al.

(10) Patent No.: US 10,828,352 B2
(45) Date of Patent: Nov. 10, 2020

(54) COMPOSITIONS AND METHODS FOR BOOSTING THE EFFICACY OF ADOPTIVE CELLULAR IMMUNOTHERAPY

(71) Applicant: Fred Hutchinson Cancer Research Center, Seattle, WA (US)

(72) Inventors: Susanna Carolina Berger, Seattle, WA (US); Stanley R. Riddell, Sammamish, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 456 days.

(21) Appl. No.: 15/521,794

(22) PCT Filed: Oct. 27, 2015

(86) PCT No.: PCT/US2015/057652
§ 371 (c)(1),
(2) Date: Apr. 25, 2017

(87) PCT Pub. No.: WO2016/069647
PCT Pub. Date: May 6, 2016

(65) Prior Publication Data
US 2017/0246279 A1    Aug. 31, 2017

Related U.S. Application Data

(60) Provisional application No. 62/069,168, filed on Oct. 27, 2014.

(51) Int. Cl.
| | |
|---|---|
| *A61K 39/00* | (2006.01) |
| *C07K 14/725* | (2006.01) |
| *A61K 39/12* | (2006.01) |
| *A61K 35/17* | (2015.01) |
| *A61K 35/15* | (2015.01) |
| *A61K 45/06* | (2006.01) |
| *C07K 14/705* | (2006.01) |
| *C07K 16/30* | (2006.01) |
| *C07K 16/28* | (2006.01) |
| *A61K 48/00* | (2006.01) |

(52) U.S. Cl.
CPC .......... *A61K 39/0011* (2013.01); *A61K 35/15* (2013.01); *A61K 35/17* (2013.01); *A61K 39/00111* (2018.08); *A61K 39/00117* (2018.08); *A61K 39/001103* (2018.08); *A61K 39/001104* (2018.08); *A61K 39/001106* (2018.08); *A61K 39/001112* (2018.08); *A61K 39/001113* (2018.08); *A61K 39/001117* (2018.08); *A61K 39/001122* (2018.08); *A61K 39/001124* (2018.08); *A61K 39/001129* (2018.08); *A61K 39/001153* (2018.08); *A61K 39/001156* (2018.08); *A61K 39/001157* (2018.08); *A61K 39/001168* (2018.08); *A61K 39/001171* (2018.08); *A61K 39/001181* (2018.08); *A61K 39/001182* (2018.08); *A61K 39/001186* (2018.08); *A61K 39/001188* (2018.08); *A61K 39/001195* (2018.08); *A61K 39/12* (2013.01); *A61K 45/06* (2013.01); *C07K 14/7051* (2013.01); *C07K 14/70578* (2013.01); *C07K 16/30* (2013.01); *A61K 48/00* (2013.01); *A61K 2039/505* (2013.01); *A61K 2039/5156* (2013.01); *A61K 2039/5158* (2013.01); *A61K 2039/54* (2013.01); *A61K 2039/545* (2013.01); *A61K 2039/55522* (2013.01); *A61K 2039/57* (2013.01); *C07K 16/2803* (2013.01); *C07K 2317/622* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,283,173 A | 2/1994 | Fields et al. | |
| 5,468,614 A | 11/1995 | Fields et al. | |
| 2004/0087025 A1 | 5/2004 | June et al. | |
| 2005/0129671 A1* | 6/2005 | Cooper | A61K 39/0011 424/93.21 |
| 2009/0324630 A1* | 12/2009 | Jensen | A61K 39/12 424/185.1 |

(Continued)

FOREIGN PATENT DOCUMENTS

| | | |
|---|---|---|
| JP | 2013-116891 A | 6/2013 |
| WO | 97/09433 | 3/1997 |
| WO | 97/41210 | 11/1997 |

(Continued)

OTHER PUBLICATIONS

Jurgens et al. (Journal of Clinical Immunology, vol. 26, No. 1, Jan. 2006) (Year: 2006).*

(Continued)

*Primary Examiner* — Zachary S Skelding
(74) *Attorney, Agent, or Firm* — Seed IP Law Group LLP

(57) ABSTRACT

The present disclosure provides compositions and methods for boosting, augmenting or enhancing the efficacy of the adoptive cellular immunotherapy by using modified T cells expressing an antigen binding protein in conjunction with modified cells (such as hematopoietic progenitor cells, modified human immune system cells or a combination thereof) expressing the antigen specifically bound by the antigen binding protein of the modified T cells.

31 Claims, 12 Drawing Sheets

(56) References Cited

U.S. PATENT DOCUMENTS

2011/0189141 A1    8/2011  Kieback et al.
2011/0243972 A1   10/2011  Jaffee

FOREIGN PATENT DOCUMENTS

| WO | 2004/035768 A1 | 4/2004 |
|---|---|---|
| WO | 2012/129514 A1 | 9/2012 |
| WO | 2014/153270 A1 | 9/2014 |
| WO | 2014/165707 A2 | 10/2014 |

OTHER PUBLICATIONS

Govers et al. (The Open Gene Therapy Journal, 2011, 4: 11-22). (Year: 2011).*
Cruz et al. (Blood. 2013;122(17):2965-2973). (Year: 2013).*
Aggen et al., "Single-chain VαVβ T-cell receptors function without mispairing with endogenous TCR chains," *Gene Therapy* 19:365-374, 2012.
Barrett et al., "Chimeric Antigen Receptor Therapy for Cancer," *Annu Rev Med.* 65:333-347, 2014. (18 pages).
Berger et al., "A nonhuman primate model for analysis of safety, persistence, and function of adoptively transferred T cells," *J Med Primatol.* 40(2):88-103, 2011. (21 pages).
Caruana Ignazio et al., "Boosting In Vivo CAR-Redirected Virus-Specific CTLs With Universal-Artificial Antigen Presenting Cells," *Blood* 122(21):4204, 2013. Database Biosis, Database AN PREV201400362624, Abstract (1 page).
Cavallo et al., "2011: the immune hallmarks of cancer," *Cancer Immunol Immunother* 60:319-326, 2011.
Chan et al., "Flow cytometric detection of degranulation reveals phenotypic heterogeneity of degranulating CMV-specific CD8+ T lymphocytes in rhesus macaques," *J. Immunol. Methods* 325(1-2):20-34, 2007. (23 pages).
Chothia et al., "The outline structure of the T-cell αβ receptor," *The EMBO Journal* 7(12):3745-3755, 1988.
Cooper et al., "Enhanced antilymphoma efficacy of CD19-redirected influenza MP1-specific CTLs by cotransfer of T cells modified to present influenza MP1," *Blood* 105(4):1622-1631, 2005.
Dossett et al., "Adoptive Immunotherapy of Disseminated Leukemia With TCR-transduced, CD8+ T Cells Expressing a Known Endogenous TCR," *Molecular Therapy* 17(4):742-749, 2009.
Hanahan et al., "Hallmarks of Cancer: The Next Generation," *Cell* 144:646-674, 2011.
Hanahan et al., "The Hallmarks of Cancer," *Cell* 100:57-70, 2000.
Hudecek et al., "The B-cell tumor-associated antigen ROR1 can be targeted with T cells modified to express a ROR1-specific chimeric antigen receptor," *Blood* 116(22):4532-4541, 2010. (18 pages).
Jiang et al. "Combination of Vaccination and Chimeric Receptor Expressing T Cells Provides Improved Active Therapy of Tumors" *The Journal of Immunology* 177:4288-4298, 2006.
Jores et al., "Resolution of hypervariable regions in T-cell receptor β chains by a modified Wu-Kabat index of amino acid diversity," *Proc. Natl. Acad. Sci. USA* 87:9138-9142, 1990.
Kalos et al., "T Cells with Chimeric Antigen Receptors Have Potent Antitumor Effects and Can Establish Memory in Patients with Advanced Leukemia," *Sci Transl Med.* 3(95):95ra73, 2011. (21 pages).
Kochenderfer et al., "Treating B-cell cancer with T cells expressing anti-CD19 chimeric antigen receptors," *Nat Rev Clin Oncol.* 10(5):267-276, 2013. (24 pages).
Kuball et al., "Facilitating matched pairing and expression of TCR chains introduced into human T cells," *Blood.* 109(6):2331-2338, 2007. (17 pages).
Kyrgidis et al., "Melanoma: Stem cells, sun exposure and hallmarks for carcinogenesis, molecular concepts and future clinical implications," *J. Carcinog.* 9:3, 2010. (26 pages).
Lamers et al., "Treatment of Metastatic Renal Cell Carcinoma With CAIX CAR-engineered T cells: Clinical Evaluation and Management of On-target Toxicity," *Molecular Therapy* 21(4):904-912, 2013.
Lou et al., "Dendritic Cells Strongly Boost the Antitumor Activity of Adoptively Transferred T Cells In vivo," *Cancer Research* 64:6783-6790, 2004.
Maus et al., "Antibody-modified T cells: CARs take the front seat for hematologic malignancies," *Blood* 123(17):2625-2635, 2014. (22 pages).
Morgan et al., "Case Report of a Serious Adverse Event Following the Administration of T Cells Transduced With a Chimeric Antigen Receptor Recognizing ERBB2," *Molecular Therapy* 18(4):843-851, 2010.
Palmer et al., "Vaccine-Stimulated, Adoptively Transferred CD8+ T Cells Traffic Indiscriminately and Ubiquitously while Mediating Specific Tumor Destruction," *J Immunol.* 173:7209-7216, 2004. (9 pages).
Park et al., "Cancer Stem Cell-Directed Therapies: Recent Data From the Laboratory and Clinic," *Molecular Therapy* 17(2):219-230, 2009.
Patel Krina K et al., "T-Cell Therapy for Multiple Myeloma Using NY-ESO-1(+) T-Cell Antigen Presenting Cells (T-APC) Combined with Adoptive Cellular Transfer (ACT) to Augment Immunotherapy," *Blood* 124(21), 2014. Database Biosis, Database AN PREV201500277242, Abstract (1 page).
Penix et al., "Two Essential Regulatory Elements in the Human Interferon Gamma Promoter Confer Activation Specific Expression in T cells," *The Journal of Experimental Medicine* 178:1483-1496, 1993.
Ribas, "Genetically Modified Dendritic Cells for Cancer Immunotherapy," *Current Gene Therapy* 5(6):619-628, 2005.
Sadelain et al., "The Basic Principles of Chimeric Antigen Receptor Design," *Cancer Discovery* 3(4):388-398, 2013. (12 pages).
Schmitt et al., "T Cell Receptor Gene Therapy for Cancer," *Human Gene Therapy* 20:1240-1248, 2009.
Stone et al., "A novel T cell receptor single-chain signaling complex mediates antigen-specific T cell activity and tumor control," *Cancer Immunol Immunother* 63:1163-1176, 2014.
Thompson et al., "cis-Acting Sequences Required for Inducible Interleukin-2 Enhancer Function Bind a Novel Ets-Related Protein, Elf-1," *Molecular and Cellular Biology* 12(3):1043-1053, 1992.
Till et al., "Adoptive immunotherapy for indolent non-Hodgkin lymphoma and mantle cell lymphoma using genetically modified autologous CD20-specific T cells," *Blood* 112(6):2261-2271, 2008. (25 pages).
Todd et al., "Transcription of the Interleukin 4 Gene Is Regulated by Multiple Promoter Elements," *J. Exp. Med.* 177:1663-1674, 1993.
Torikai et al., "A foundation for universal T-cell based immunotherapy: T cells engineered to express a CD19-specific chimeric-antigen-receptor and eliminate expression of endogenous TCR," *Blood* 119(24):5697-5705, 2012. (10 pages).
Wang Xiuli et al., "Enhanced Antitumor Efficacy of Adoptively Transferred CD19-Redirected CMV Specific Central Memory T Cells by CMV Vaccine," *Blood* 120(21):3014, 2012. Database Biosis, Database AN PREV201300229759, Abstract (1 page).
Wolff et al., "Monoclonal Antibody Enhanced Antitumor Activity in Nude Mice," *Cancer Research* 53:2560-2565, 1993. (7 pages).
International Search Report and Written Opinion dated Jan. 27, 2016, in corresponding PCT Application No. PCT/US2015/057652, 15 pages.
International Preliminary Report on Patentability dated May 2, 2017, in corresponding PCT Application No. PCT/US2015/057652, 8 pages.
Bear et al., "T Cells as Vehicles for Cancer Vaccination," *Journal of Biomedicine and Biotechnology*, 2011. (8 pages).
Berger et al., "Safety of targeting ROR1 in primates with chimeric antigen receptor-modified T cells," *Cancer Immunol Res.* 3(2):206-216, 2015. (24 pages).
Carreno et al., "A dendritic cell vaccine increases the breadth and diversity of melanoma neoantigen-specific T cells," *Science* 348(6236):803-808, 2015. (8 pages).
Chmielewski et al., "Antigen-specific T-cell activation independently of the MHC: chimeric antigen receptor-redirected T cells," *Frontiers in Immunology* 4(371), 2013. (7 pages).

(56) References Cited

OTHER PUBLICATIONS

Cho et al., "CD4 T cells transduced with CD80 and 4-1BBL mRNA induce long-term CD8 T cell responses resulting in potent antitumor effects," *Journal for ImmunoTherapy of Cancer* 2(3):264, 2014.

Fontana et al., "Peripheral blood lymphocytes genetically modified to express the self/tumor antigen MAGE-A3 induce antitumor immune responses in cancer patients," *Blood* 113(8):1651-1660, 2009. (11 pages).

Kreiter et al., "Mutant MHC class II epitopes drive therapeutic immune responses to cancer," *Nature* 520:692-696, 2015. (17 pages).

Kyte et al., "Phase I/II trial of melanoma therapy with dendritic cells transfected with autologous tumor-mRNA," *Cancer Gene Therapy* 13:905-918, 2006.

Liang et al., "In vitro induction of specific anti-tumoral immunity against laryngeal carcinoma by using human interleukin-12 gene-transfected dendritic cells," *Chinese Medical Journal* 124(9):1357-1361, 2011.

Maher, "Immunotherapy of Malignant Disease Using Chimeric Antigen Receptor Engrafted T Cells," *ISRN Oncology*, 2012. (23 pages).

Melief, "'License to Kill' Reflects Joint Action of CD4 and CD8 T Cells," *Clin Cancer Res* 19(16):4295-4296, 2013. (3 pages).

Nakazawa et al., "Optimization of the PiggyBac Transposon System for the Sustained Genetic Modification of Human T-Lymphocytes," *J Immunother.* 32(8):826-836, 2009. (18 pages).

Russo et al., "Clinical and immunologic responses in melanoma patients vaccinated with MAGE-A3-genetically modified lymphocytes," *International Journal of Cancer* 132:2557-2566, 2013.

Russo et al., "Lymphocytes genetically modified to express tumor antigens target DCs in vivo and induce antitumor immunity," *The Journal of Clinical Investigation* 117(10):3087-3096, 2007.

Sun et al., "Listeriolysin O as a strong immunogenic molecule for the development of new anti-tumor vaccines," *Human Vaccines & Immunotherapeutics* 9(5): 1058-1068, 2013.

Tanimoto et al., "Genetically engineered fixed K562 cells: potent "off-the-shelf" antigen-presenting cells for generating virus-specific T cells," *Cytotherapy* 16:135-146, 2014.

Toobiak et al., "Carbon Monoxide Induced Erythroid Differentiation of K562 Cells Mimics the Central Macrophage Milieu in Erythroblastic Islands," *PLoS One* 7(3):e33940, 2012. (8 pages).

Wilgenhof et al., "Therapeutic Vaccination With an Autologous mRNA Electroporated Dendritic Cell Vaccine in Patients With Advanced Melanoma," *J Immunother* 34(5):448-456, 2011.

Zhang et al., "Optimizing DC Vaccination by Combination With Oncolytic Adenovirus Coexpressing IL-12 and GM-CSF," *Molecular Therapy* 19(8):1558-1568, 2011.

* cited by examiner

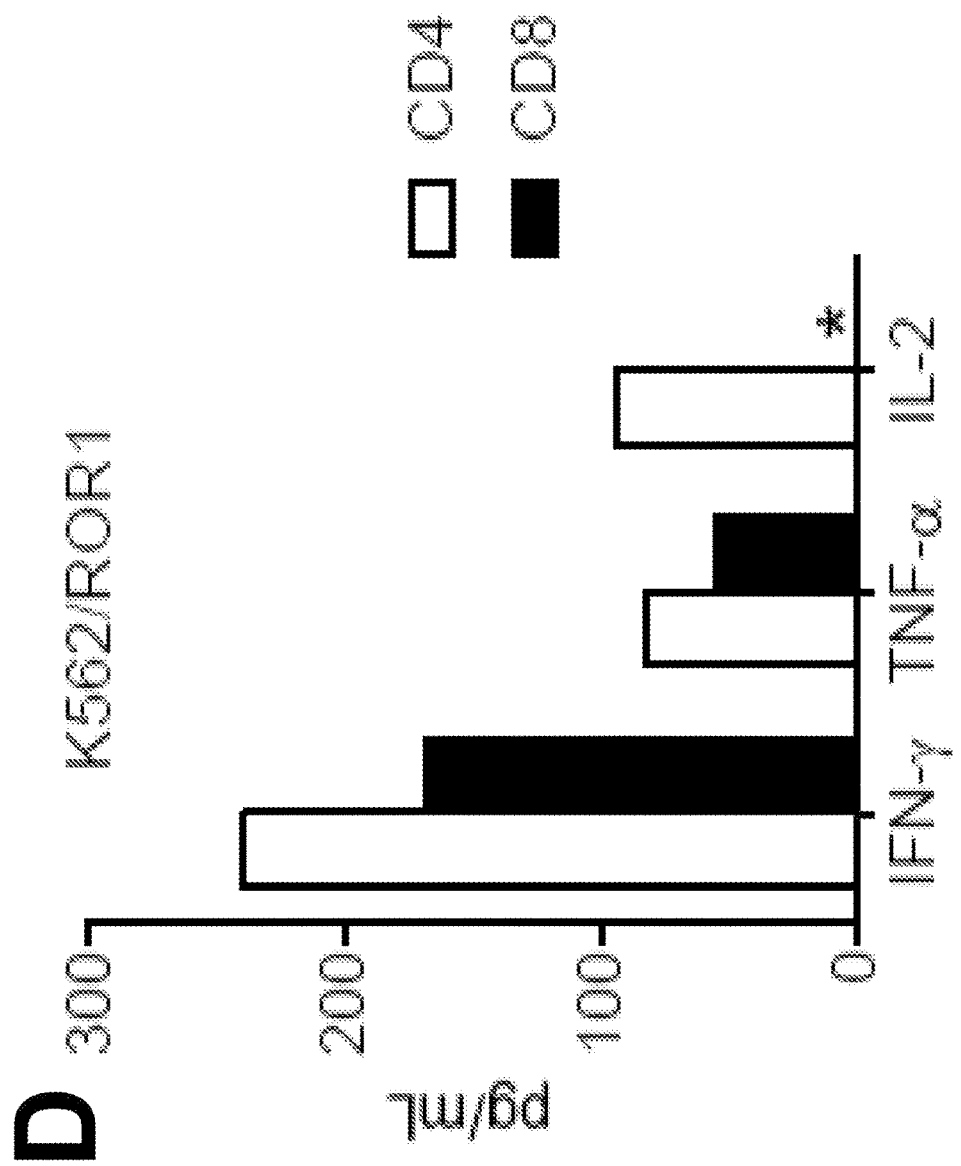

COMPOSITIONS AND METHODS FOR BOOSTING THE EFFICACY OF ADOPTIVE CELLULAR IMMUNOTHERAPY

CROSS REFERENCE TO RELATED APPLICATION

This application claims the benefit under 35 U.S.C. § 119(e) to U.S. Provisional Application 62/069,168 filed Oct. 27, 2014, which application is incorporated by reference herein in its entirety.

STATEMENT OF GOVERNMENT INTEREST

This invention was made with government support under CA114536, and AI053193 awarded by the National Institutes of Health. The government has certain rights in this invention.

BACKGROUND

Technical Field

The present disclosure relates generally to compositions and methods for enhancing or boosting the efficacy of an immunotherapy. More specifically, the present disclosure relates to using a T cell expressing an antigen binding protein (e.g., chimeric antigen receptor) in conjunction with cells (such as hematopoietic progenitor cells, modified human immune system cells or a combination thereof) modified to express the antigen specifically bound by the antigen binding protein of the modified T cells to boost adoptive cellular immunotherapy for treating diseases or disorders associated with expression of the targeted antigen, such as cancer.

Description of the Related Art

The introduction of tumor-targeting receptors into T cells by gene transfer allows the rapid generation of tumor-specific T cells from any cancer patient for adoptive T-cell therapy. A promising strategy involves engineering T cells with synthetic chimeric antigen receptors (CARs) comprised of a single chain antibody or other binding domain that is specific for a tumor cell-surface molecule and is linked to one or more T-cell signaling molecules (Turtle et al., *Curr. Opin. Immunol.* 24:633, 2012; Barrett et al., *Annu. Rev. Med.* 65:10.1, 2014; Sadelain et al., *Cancer Discovery* 3:388, 2013). Recent trials using CAR-modified T cells (CAR-T cells) specific for the CD19 molecule on B-cell malignancies demonstrated marked tumor regression in a subset of patients with advanced disease (Barrett et al., 2014; Sadelain et al., 2013; Kalos et al., *Sci. Transl. Med.* 3:95ra73, 2011; Kochenderfer and Rosenberg, *Nat. Rev. Clin. Oncol.* 10:267, 2013). Extending this therapy to common epithelial cancers poses several challenges, including the identification of molecules expressed on tumor cells that can be targeted safely with T cells. This is underscored by serious and even fatal toxicities that have been observed due to on-target/off-tumor effects of CAR-therapy on normal cells that express the target molecule (Lamers et al., *Mol. Ther.* 21:904, 2013; Morgan et al., *Mol. Ther.* 18:843, 2010). In addition, being able to identify the properties of T cells that dictate their ability to survive and function in vivo remain important areas of research.

Clearly there is a need for alternative compositions and methods to enhance or boost adoptive cellular immunotherapies directed against various cancers, such as leukemia and tumors. The presently disclosed embodiments address this need and provide other related advantages.

BRIEF DESCRIPTION OF THE DRAWINGS

FIGS. 1A-1D show function and characterization of Rhesus macaque ROR1. (A) function of rhesus macaque T cells modified to express a R12-ROR1 CAR with human or macaque 4-1BB and CD3ζ domains. (B) flow cytometric analysis of purity and phenotype of ROR1 CAR-modified CD4$^+$ and CD8$^+$ T cells using the tCD19 marker. The data shows the phenotype of untransduced T cells (mock), transduced T cells pre and post selection on tCD19 and post selection on CD4 (top panels) or CD8 (bottom panels). All samples are gated on CD3$^+$ cells. (C) cytolytic activity of CD4$^+$ and CD8$^+$ ROR1 CAR-T cells against $^{51}$Cr-labeled K562/ROR1 or K562 cells in a 4-hour cytotoxicity assay. (D) Luminex cytokine assay of supernatants obtained after 24 hours from triplicate co-cultures of 5×10$^4$ ROR1 CAR-T cells with K562/ROR1 cells or PMA/Ionomycin, or media alone as described in Methods. Cytokine levels in the media control samples were below the detection level. B-D, shows data from macaque A13002 that are representative of independent experiments in 3 animals.

DETAILED DESCRIPTION

Figure 1A:
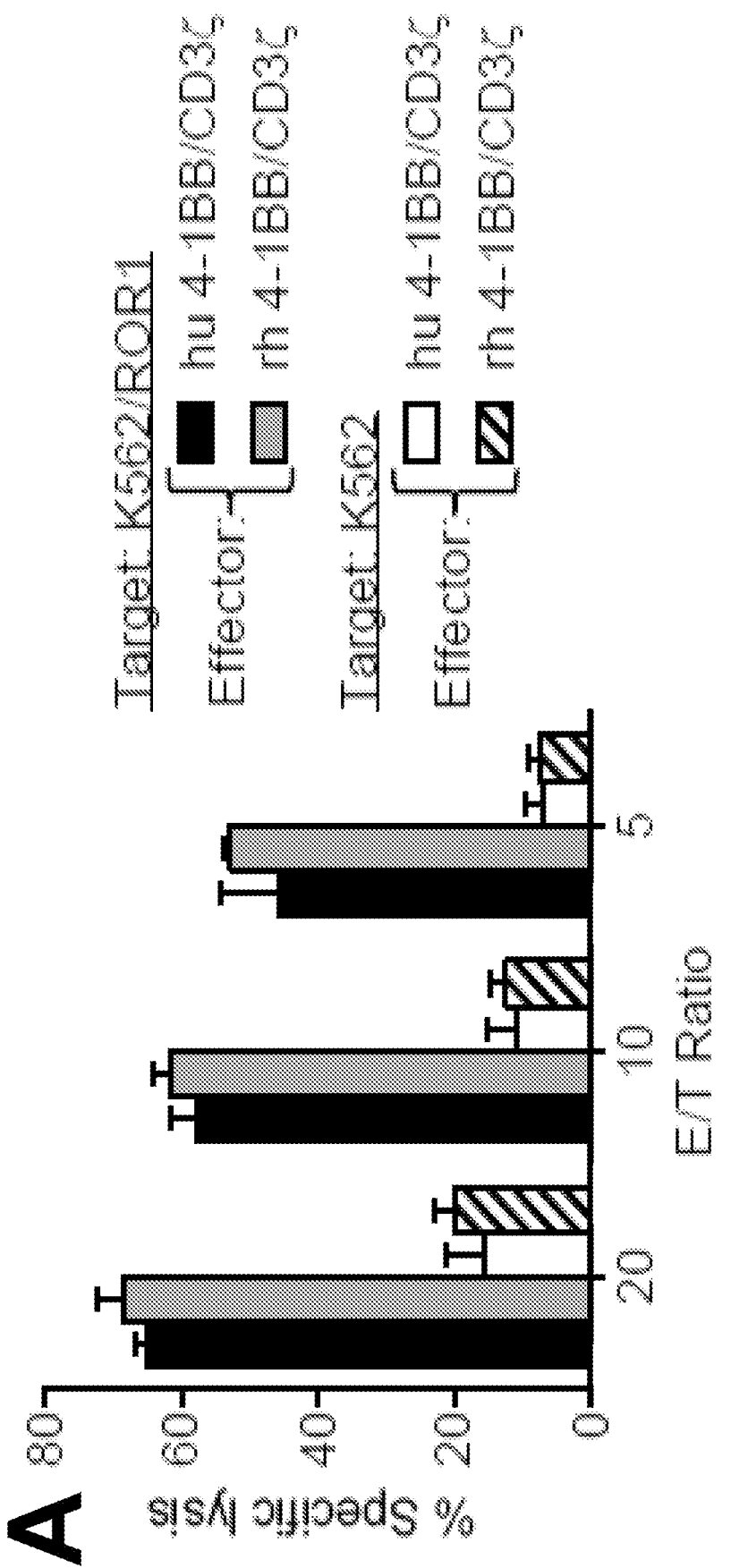

In one aspect, the present disclosure provides compositions and methods for boosting, augmenting or enhancing the efficacy of adoptive cellular immunotherapy or treating a hyperproliferative disorder by administering to human subject an effective amount of a composition comprising a population of modified human T cells comprising a nucleic acid molecule that encodes an antigen binding protein (e.g., chimeric antigen receptor, CAR), wherein the antigen binding protein comprises a hydrophobic portion disposed between an extracellular binding component and an intracellular effector component; and a population of modified human hematopoietic progenitor cells, modified human immune system cells or a combination thereof comprising a nucleic acid molecule that encodes the antigen specifically recognized by the extracellular binding component of the antigen binding protein.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a CD24$^{Lo}$ Lin$^-$ CD117$^+$ phenotype or those found in the thymus (referred to as progenitor thymocytes).

"Hematopoietic stem cells" refer to undifferentiated hematopoietic cells that are capable of self-renewal either in vivo, essentially unlimited propagation in vitro, and capable of differentiation to other cell types including cells of the T cell lineage. Hematopoietic stem cells may be isolated, for example, from fetal liver, bone marrow, cord blood.

"Embryonic stem cells" or "ES cells" or "ESCs" refer to undifferentiated embryonic stem cells that have the ability to integrate into and become part of the germ line of a developing embryo. Embryonic stem cells are capable of differentiating into hematopoietic progenitor cells, and any tissue or organ. Embryonic stem cells that are suitable for use herein include cells from the J1 ES cell line, 129J ES cell line, murine stem cell line D3 (American Type Culture Collection), the R1 or E14K cell lines derived from 129/Sv mice, cell lines derived from Balb/c and C57B1/6 mice, and human embryonic stem cells (e.g., from WiCell Research Institute, WI; or ES cell International, Melbourne, Australia).

As used herein, an "immune system cell" means any cell of the immune system that originate from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include CD4+ T cells, CD8+ T cells, CD4− CD8− double negative T cells, γδ T cells, regulatory T cells, natural killer cells, and dendritic cells. Macrophages and dendritic cells may be referred to as "antigen presenting cells" or "APCs," which are specialized cells that can activate T cells when a major histocompatibility complex (MHC) receptor on the surface of the APC interacts with a TCR on the surface of a T cell. Alternatively, any hematopoietic stem cell or immune system cell can be converted into an APC by introducing a nucleic acid molecule that expresses an antigen recognized by the TCR or by another antigen binding protein (e.g., CAR)

As used herein, the term "host" refers to a cell (e.g., T cell, hematopoietic progenitor cell) or microorganism targeted for genetic modification with a heterologous or exogenous nucleic acid molecule to produce a polypeptide of interest (e.g., cancer antigen-specific CAR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated CD34; increased co-stimulatory factor expression). In certain embodiments, a host cell is a human hematopoietic progenitor cell transduced with heterologous or exogenous nucleic acid molecule encoding an antigen associated with disease and specifically bound by an antigen binding protein (e.g., CAR).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to a antigen-experienced CD8+ cytotoxic T lymphocytes that has decreased expression of CD62L, CCR7, CD28, and are positive for granzyme and perforin as compared to $T_{CM}$.

A "binding component" (also referred to as a "binding region" or "binding moiety"), as used herein, refers to a peptide, oligopeptide, polypeptide, or protein that possesses the ability to specifically and non-covalently associate, unite, or combine with a target molecule (e.g., CD19, CD20, EGFRvIII, GD2, MUC16, ROR1, mesothelin, PD-L1, PD-L2, PSMA, cancer-associated neoantigen). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for the specific ability to bind to a biological molecule, a molecular complex or other target of interest.

As used herein, "specifically binds" or "specific for" refers to an association or union of a binding protein (e.g., CAR or TCR) or a binding component (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

As used herein, a "hinge region" or a "hinge" refers to (a) an immunoglobulin hinge sequence (made up of, for example, upper and core regions) or a functional variant thereof, (b) a type II C-lectin interdomain (stalk) region or a functional variant thereof, or (c) a cluster of differentiation (CD) molecule stalk region or a functional variant thereof. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a hinge region is human, and in particular embodiments, comprises a human IgG hinge region.

A "hydrophobic portion," as used herein, means any amino acid sequence having a three-dimensional structure that is thermodynamically stable in a cell membrane, and generally ranges in length from about 15 amino acids to about 30 amino acids. The structure of a hydrophobic domain may comprise an alpha helix, a beta barrel, a beta sheet, a beta helix, or any combination thereof.

As used herein, an "effector component" or "effector domain" is an intracellular portion of a fusion protein or receptor that can directly or indirectly promote a biological or physiological response in a cell when receiving the appropriate signal. In certain embodiments, an effector component is part of a protein, fusion protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector component will indirectly promote a cellular response by associating with one or more other proteins that directly promote a cellular response.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids. In further embodiments, a linker is a variable region linker that connects a heavy chain immunoglobulin variable region to a light chain immunoglobulin variable region or connects T cell receptor $V_{\alpha\alpha\beta}$ and $C_{\alpha/\beta}$ chains (e.g., $V_\alpha$-$C_\alpha$, $V_\beta$-$C_\beta$, $V_\alpha$-$V_\beta$) or connects each $V_\alpha$-$C_\alpha$, $V_\beta$-$C_\beta$, $V_\alpha$-$V_\beta$ pair to a hinge or hydrophobic domain.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered component" or "altered domain" or "altered protein" refers to a motif, region, domain, peptide, polypeptide, or protein with a sequence identity to a wild type motif, region, domain, peptide, polypeptide, or protein (e.g., wild type intracellular domains CD3ζ, CD134, CD137) of at least 85% (e.g., 86%, 87%, 88%, 89%, 90%, 91%, 92%, 93%, 94%, 95%, 96%, 97%, 98%, 99%, or 99.5%).

As used herein, an "antigen" encoded by nucleic acid molecule contained in a modified human hematopoietic progenitor cells, modified human immune system cells or a combination thereof refers to any biological molecule (e.g., protein, carbohydrate) that is associated with a disease or disorder (e.g., cancer) and targeted for immunotherapy. In certain embodiments, antigen may be an anti-idiotype antibody or anti-idiotype antibody binding fragment thereof, or an antibody or antibody binding fragment thereof specific for an antigen binding protein (e.g., CAR) expressed by a modified T cell. Exemplary antigens include α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFRβ, LRP5, MAGE, mesothelin, MUC1, NY-ESO-1, a cancer-specific neoantigen, OSMRβ, PD1, PD-L1, PD-L2, PSMA, PTCH1, RANK, Robo1, ROR1, TERT, TGFBR2, TGFBR1, TLR7, TLR9, TNFRSF4, TNFR1, TNFR2, tyrosinase, TWEAK-R, or WT-1.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, $3^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRα, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_a$, β-chain variable domain or $V_\beta$; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_\alpha$ typically amino acids 117 to 259 based on Kabat, β-chain constant domain or $C_\beta$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3δ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of C3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3δ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the term "recombinant" refers to a cell, microorganism, nucleic acid molecule, or vector that has been modified by introduction of an exogenous nucleic acid molecule, or refers to a cell or microorganism that has been altered such that expression of an endogenous nucleic acid molecule or gene is controlled, deregulated or constitutive, where such alterations or modifications may be introduced by genetic engineering. Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp. 71-77, 1975; Lewin, Genes IV, Oxford University Press, NY and Cell Press, Cambridge, Mass., p. 8, 1990).

The term "construct" refers to any polynucleotide that contains a recombinant nucleic acid. A construct may be present in a vector (e.g., a bacterial vector, a viral vector) or may be integrated into a genome. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired antigen-specific binding proteins (e.g., CAR, TCRα and TCRβ). When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, "hyperproliferative disorder" refers to excessive growth or proliferation as compared to a normal or undiseased cell. Exemplary hyperproliferative disorders include tumors, cancers, neoplastic tissue, carcinoma, pre-malignant cells, as well as non-neoplastic or non-malignant hyperproliferative disorders (e.g., adenoma, fibroma, lipoma, leiomyoma, hemangioma, restenosis, as well as autoimmune diseases such as rheumatoid arthritis, osteoarthritis, psoriasis, inflammatory bowel disease, or the like).

Modified Cells Expressing Antigen Binding Protein or Antigen

In certain aspects, the instant disclosure provides an adoptive cellular immunotherapy composition, comprising a population of modified human hematopoietic progenitor cells, modified human immune system cells or a combination thereof, wherein a first population of modified cells are T cells comprising a nucleic acid molecule that encodes an antigen binding protein (e.g., CAR), and a second population of modified cells comprising a nucleic acid molecule that encodes the antigen (e.g., cancer-specific antigen, anti-idiotypic antibody or binding fragment thereof). In these embodiments, the antigen binding protein comprises a hydrophobic portion disposed between an extracellular binding component and an intracellular effector component, and the extracellular binding component is specific for the antigen encoded by the second population of modified cells. For example, an antigen binding protein may be a T cell receptor (TCR) or a chimeric antigen receptor.

An advantage of these compositions is that a lower dose of, for example, an antigen-specific CAR T cell may be administered to a patient, and then administering (e.g., simultaneously or sequentially) a second population of cells expressing the antigen recognized by the CAR will boost the effect of the adoptive immunotherapy. Another advantage is that the boosting effect can also improve homing so the cells migrate to the tissue of interest. Yet another advantage of the combination of a CAR expressing T cell and an artificial APC is to systemically boosting the effect of the adoptive immunotherapy in order to get more active cells at the site of the tumor.

In certain other aspects, a modified hematopoietic progenitor cell comprising a nucleic acid molecule that encodes the antigen is administered to a subject, wherein the encoded antigen is under the control of a regulated promoter. The modified hematopoietic progenitor cell will locate in a tissue of interest and replicate (e.g., bone marrow or lymph nodes). Then, the expression of antigen in the expanded modified hematopoietic progenitor cells may be induced simultaneous with or just after the subject is administered a first population of modified cells T cells comprising a nucleic acid molecule that encodes an antigen binding protein (e.g., CAR), wherein the number of introduced "APCs" is much greater than would be available by ex vivo expansion and administration. In certain embodiments, the administered second population of cells is irradiated before administration.

In any of the aforementioned embodiments, the antigen binding protein comprises binding component, a hydrophobic portion and an intracellular effector component. For example the binding component may be an antibody variable fragment (Fv), a TCR variable domain, a receptor ectodomain, or a ligand. In further embodiments, the binding component is a scFv or scTCR comprising a variable region linker, such as a linker comprises a $(Gly_xSer_y)_n$, wherein x and y are independently an integer from 1 to 5, and n is an integer from 1 to 10. In further embodiments, the binding component is specific for α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFRβ, LRP5, MAGE, mesothelin, MUC1, NY-ESO-1, a cancer-specific neoantigen, OSMRβ, PD1, PD-L1, PD-L2, PSMA, PTCH1, RANK, Robo1, ROR1, TERT, TGFBR2, TGFBR1, TLR7, TLR9, TNFRSF4, TNFR1, TNFR2, tyrosinase, TWEAK-R, or WT-1.

In still further embodiments, the hydrophobic portion is a transmembrane domain, such as a CD4, CD8, CD28 or CD27 transmembrane domain.

In certain embodiments, an intracellular effector component comprises an intracellular region of CD38, CD36, CD3C, CD25, CD27, CD28, CD79A, CD79B, CD134, CD137, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, ROR2, Ryk, SLAMF1, Slp76, pTα, TCRα, TCRβ, TRIM, Zap70, PTCH2, or any combination thereof. In particular embodiments, the intracellular effector component comprises CD3ζ and one or more of CD27, CD28, CD134, and CD137, or the intracellular effector component comprises LRP, NOTCH1, NOTCH2, NOTCH3, NOTCH4, ROR2, or Ryk.

In any of the aforementioned embodiments, the modified cell is an immune system cell, such as a CD4+ T cell, a CD8+ T cell, a CD4− CD8− double negative T cell, a γδ T cell, regulatory T cell, a natural killer cell, a dendritic cell, or any combination thereof. In certain embodiments, the T cell is a naïve T cell, a central memory T cell, an effector memory T cell, or any combination thereof. For example, the first population of modified T cells may consist essentially of CD4+ T cells, CD8+ T cells, or both CD4+ and CD8+ T cells, and the second population of modified cells comprises modified human hematopoietic progenitor cells. In other examples, the first population of modified T cells may consist essentially of CD4+ T cells, CD8+ T cells, or both CD4+ and CD8+ T cells, and the second population of modified cells comprises modified human immune system cells, such as cells consisting essentially of CD4+ T cells, a CD8+ T cells, or both CD4+ and CD8+ T cells.

In any of the aforementioned embodiments, the modified cell populations are recombinantly modified ex vivo by use of, for example, a viral vector, such as a lentiviral vector or a γ-retroviral vector. In further embodiments, the cell populations being modified are syngeneic, allogeneic, or autologous cells. In any of the aforementioned embodiments, the modified cell populations are further formulated with a pharmaceutically acceptable carrier, diluent, or excipient as described herein.

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, an antigen specific binding protein a binding component that is at least about 90% or at least about 95% identical to an amino acid sequence to the original wild type sequence, provided that (a) at least three or four of the CDRs have no mutations and (b) the CDRs that do have mutations have only up to two or three amino acid substitutions, up to a contiguous five amino acid deletion, or a combination thereof.

In certain embodiments, nucleic acid molecules encoding an antigen binding protein or antigen are used to transfect/transduce a host cell (e.g., hematopoietic stem cells, T cells) for use in adoptive transfer therapy. Recent advances in methods for transfecting/transducing T-cells with desired nucleic acids have been described (e.g., US 2004/0087025), as have adoptive transfer procedures using T-cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US2011/0189141; Leen et al., *Ann. Rev. Immunol.* 25:243, 2007), such that adaptation of these methodologies to the presently disclosed embodiments is contemplated, based on the teachings herein.

The antigen binding proteins or components as described herein may be functionally characterized according to any of a large number of art accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein).

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Polynucleotides Encoding Antigen Binding Proteins or Antigens

Isolated or recombinant nucleic acid molecules encoding an antigen binding protein like a CAR, high affinity recombinant TCR specific for antigen, or the antigen or an anti-idiotypic antibody against the antigen specific binding component as described herein may be produced and prepared according to various methods and techniques of the molecular biology or polypeptide purification arts. Construction of an expression vector that is used for recombinantly producing an antigen binding protein like a CAR, high affinity recombinant TCR specific for antigen, or the antigen or an anti-idiotypic antibody against the antigen specific binding component of interest can be accomplished by using any suitable molecular biology engineering techniques known in the art, including the use of restriction endonuclease digestion, ligation, transformation, plasmid purification, and DNA sequencing, for example as described in Sambrook et al. (1989 and 2001 editions; *Molecular Cloning: A Laboratory Manual*, Cold Spring Harbor Laboratory Press, NY) and Ausubel et al. (Current Protocols in Molecular Biology (2003)). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen. In certain embodiments, a polynucleotide is codon optimized for efficient expression in a target host cell.

Certain embodiments relate to nucleic acids that encode the polypeptides contemplated herein, for instance, chimeric antigen receptors, high affinity recombinant TCRs, the antigen of interest and anti-idiotypic antibodies specific for the antigen binding proteins. As one of skill in the art will recognize, a nucleic acid may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA—DNA hybrids, ribozymes, and other various naturally occurring or synthetic forms of DNA or RNA.

Standard techniques may be used for recombinant DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols* (*Methods in Molecular Biology*) (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Certain embodiments include nucleic acids contained in a vector. One of skill in the art can readily ascertain suitable vectors for use with certain embodiments disclosed herein. A typical vector may comprise a nucleic acid molecule capable of transporting another nucleic acid to which it has been linked, or which is capable of replication in a host organism. Some examples of vectors include plasmids, viral vectors, cosmids, and others. Some vectors may be capable of autonomous replication in a host cell into which they are introduced (e.g., bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked (these vectors may be referred to as "expression vectors"). According to related embodiments, it is further understood that, if one or more agents (e.g., polynucleotides encoding an antigen binding protein like a CAR, high affinity recombinant TCR specific for antigen, or the antigen or an anti-idiotypic antibody against the antigen specific binding component, as described herein) is co-administered to a subject, that each agent may reside in separate or the same vectors, and multiple vectors (each containing a different agent the same agent) may be introduced to a cell or cell population or administered to a subject.

In certain embodiments, the nucleic acid encoding antigen binding proteins or antigens of this disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In particular embodiments, the recombinant expression vector is delivered to an appropriate cell, for example, a hematopoietic stem cell, T cell, antigen-presenting cell (e.g., a dendritic cell) or the like. The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. For example, see Sambrook et al., *Molecular Cloning: A Laboratory Manual* 2d ed. (Cold Spring Harbor Laboratory, 1989).

Methods of Treatment

In certain aspects, the instant disclosure is directed to methods for treating a hyperproliferative disorder or a condition (e.g., characterized by antigen overexpression) by administering to human subject an effective amount of a composition comprising a population of modified human T cells comprising a nucleic acid molecule that encodes an antigen binding protein, wherein the antigen binding protein comprises a hydrophobic portion disposed between an extracellular binding component and an intracellular effector component; and a population of modified human hematopoietic progenitor cells, modified human immune system cells or a combination thereof comprising a nucleic acid molecule that encodes the antigen specifically recognized by the extracellular binding component of the antigen binding protein. In certain embodiments, the administration steps may be repeated multiple times and for a period of a few weeks, a few months, or up to two years or more.

In certain embodiments, the hyperproliferative disorder is a hematological malignancy or a solid cancer. Exemplary hematological malignancies include acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), or multiple myeloma (MM). Exemplary solid cancers include biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In further aspects, the instant disclosure is directed to a for treating a disease in a subject by (a) administering to a subject an effective amount of a population of modified human T cells comprising a nucleic acid molecule that encodes an antigen binding protein, wherein the antigen binding protein comprises a hydrophobic portion disposed between an extracellular binding component and an intracellular effector component; (b) administering to the subject an effective amount of a population of modified human hematopoietic progenitor cells, modified human immune system cells or a combination thereof comprising a nucleic acid molecule that encodes the antigen, wherein the extracellular binding component of the antigen binding protein from the modified human T cells of step (a) is specific for the antigen encoded by the population of modified cells of this step (b); and (c) optionally repeating step (a), step (b) or both steps (a) and (b); thereby treating disease by adoptive cellular immunotherapy.

In still further aspects, the instant disclosure is directed to a method for improving adoptive cellular immunotherapy by (a) administering to a subject an effective amount of a population of modified human T cells comprising a nucleic acid molecule that encodes an antigen binding protein, wherein the antigen binding protein comprises a hydrophobic portion disposed between an extracellular binding component and an intracellular effector component; and (b) administering to the subject an effective amount of a population of modified human hematopoietic progenitor cells, modified human immune system cells or a combination thereof comprising a nucleic acid molecule that encodes the antigen, wherein the extracellular binding component of the antigen binding protein from the modified human T cells of step (a) is specific for the antigen encoded by the population of modified cells of this step (b). These administrations, which may be repeated as described herein, thereby boost, augment or enhance the efficacy of the adoptive cellular immunotherapy.

In any of the aforementioned embodiments, the methods are used to treat a viral disease, a bacterial disease, a cancer, an inflammatory disease, an immune disease, or an aging-associated disease.

In any of the aforementioned embodiments, the methods are used with cells encoding an antigen binding protein comprising a binding component, a hydrophobic portion and an intracellular effector component. For example the binding component may be an antibody variable fragment (Fv), a TCR variable domain, a receptor ectodomain, or a ligand. In further embodiments, the binding component is a scFv or scTCR comprising a variable region linker, such as a linker comprises a $(Gly_xSer_y)_n$, wherein x and y are independently an integer from 1 to 5, and n is an integer from 1 to 10. In further embodiments, the binding component is specific for α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFRβ, LRP5, MAGE, mesothelin, MUC1, NY-ESO-1, a cancer-specific neoantigen, OSMRβ, PD1, PD-L1, PD-L2, PSMA, PTCH1, RANK, Robo1, ROR1, TERT, TGFBR2, TGFBR1, TLR7, TLR9, TNFRSF4, TNFR1, TNFR2, tyrosinase, TWEAK-R, or WT-1. In any of these embodiments, the extracellular binding component of the antigen binding protein from the modified human T cells is directed against a disease cell overexpressing the antigen.

In still further embodiments, the hydrophobic portion is a transmembrane domain, such as a CD4, CD8, CD28 or CD27 transmembrane domain. In certain embodiments, an intracellular effector component comprises an intracellular region of CD3ε, CD3δ, CD3ζ, CD25, CD27, CD28, CD79A, CD79B, CD134, CD137, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, ROR2, Ryk, SLAMF1, Slp76, pTα, TCRα, TCRβ, TRIM, Zap70, PTCH2, or any combination thereof. In particular embodiments, the intracellular effector component comprises CD3ζ and one or more of CD27, CD28, CD134, and CD137, or the intracellular effector component comprises LRP, NOTCH1, NOTCH2, NOTCH3, NOTCH4, ROR2, or Ryk.

In any of the aforementioned embodiments, the methods provide the use of a modified immune system cell, such as a CD4+ T cell, a CD8+ T cell, a CD4– CD8– double negative T cell, a γδ T cell, regulatory T cell, a natural killer cell, a dendritic cell, or any combination thereof. In certain embodiments, the T cell is a naïve T cell, a central memory T cell, an effector memory T cell, or any combination thereof. For example, the first population of modified T cells may consist essentially of CD4+ T cells, CD8+ T cells, or both CD4+ and CD8+ T cells, and the second population of modified cells comprises modified human hematopoietic progenitor cells. In other examples, the first population of modified T cells may consist essentially of CD4+ T cells, CD8+ T cells, or both CD4+ and CD8+ T cells, and the second population of modified cells comprises modified human immune system cells, such as cells consisting essentially of CD4+ T cells, a CD8+ T cells, or both CD4+ and CD8+ T cells.

In any of the aforementioned embodiments, the methods provide the use of modified cell populations that are recombinantly modified ex vivo via, for example, a viral vector, such as a lentiviral vector or a γ-retroviral vector. In further embodiments, the cell populations being modified are syngeneic, allogeneic, or autologous cells. In any of the aforementioned embodiments, the modified cell populations are further formulated with a pharmaceutically acceptable carrier, diluent, or excipient as described herein.

In any of the aforementioned embodiments, the methods comprise administering the modified cell populations intravenously.

In any of the aforementioned embodiments, the methods comprise administering to the subject a plurality of doses of the modified T cells from step (a), a plurality of doses of modified cells from step (b), or a combination thereof. For example, the plurality of doses of modified T cells from step (a) are administered at intervals between administrations of about one week to about four weeks. In certain embodiments, the modified T cells from step (a) are administered concurrently or sequentially with the modified cells from step (b). In further embodiments, the initial dose of modified cells from step (b) are administered from about 1 day to about 28 days after administering the modified T cells from step (a).

In any of the aforementioned embodiments, the methods comprise administering the modified cells from step (b) sequentially within about 24 hours of administering the modified T cells from step (a), or the modified T cells from step (a) sequentially within about 24 hours of administering the modified cells from step (b). In a specific embodiment, the initial administration comprises administering a composition comprising a mixture of the modified T cells from step (a) and the modified cells from step (b), provided that the cells from step (b) are not activating the cells from step (a) until the mixture is administered to a subject. In further embodiments, the modified cells from step (b) are further administered in one or more doses at one or more intervals for up to about 365 days after administering the modified T cells from step (a). In any of the aforementioned embodiments, the modified cells from step (b) comprise or consist essentially of modified hematopoietic progenitor cells, or comprise or consist essentially of T cells.

In any of the aforementioned embodiments, the modified T cells from step (a) are administered to the subject at a dose of about $10^6$ cells/m$^2$ to about $10^{11}$ cells/m$^2$ and the modified T cells from step (b) are administered to the subject at a dose of about $10^6$ cells/m$^2$ to about $10^{11}$ cells/m$^2$, wherein the doses for either or both modified cell populations may be repeated as described herein.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., Park et al., *Molec. Therap.* 17:219, 2009).

In another aspect, the present disclosure provides a method for inhibiting growth, metastasis or metastatic growth of a malignancy (e.g., a solid malignancy or a hematologic malignancy), comprising administering to a subject in need thereof an effective amount of a cell encoding a polypeptide complex provided herein or a composition thereof.

A wide variety of cancers, including solid malignancy and hematologic malignancy, are amenable to the compositions and methods disclosed herein. Types of cancer that may be treated include adenocarcinoma of the breast, prostate, pancreas, colon and rectum; all forms of bronchogenic carcinoma of the lung (including squamous cell carcinoma, adenocarcinoma, small cell lung cancer and non-small cell lung cancer); myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; non-Hodgkin's lymphoma; plasmacytoma; reticuloendotheliosis; melanoma; renal cell carcinoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; and glioblastoma multiforme. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Additional exemplary cancers that are also amenable to the compositions and methods disclosed herein are B-cell cancers, including B-cell lymphomas [such as various forms of Hodgkin's disease, non-Hodgkin's lymphoma (NHL) or central nervous system lymphomas], leukemias [such as acute lymphoblastic leukemia (ALL), chronic lymphocytic leukemia (CLL), Hairy cell leukemia and chronic myoblastic leukemia] and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

In certain embodiments, cells encoding antigen binding proteins useful for inhibiting growth of a solid malignancy or metastasis or metastatic growth of a solid malignancy or a hematologic malignancy include those that specifically bind to a tumor or cancer antigen and a second target antigen on the cancer cell.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of an antigen binding protein (e.g., CAR) or high affinity recombinant TCR specific for a human target antigen a host T cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

Cells expressing an antigen binding protein or high affinity recombinant TCR specific for human disease-associated antigen, along with cells expressing the target antigen, as described herein, may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose is an amount of host T cells (expressing an antigen binding protein or high affinity recombinant TCR specific for a human disease-associated antigen) and cells expressing the target antigen used in adoptive transfer that is capable of producing a clinically desirable result (i.e., a sufficient amount to induce or enhance a specific T cell immune response against cells overexpressing antigen (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^6$ cells/m$^2$, about $5\times10^6$ cells/m$^2$, about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with antigen overexpression includes any disorder or condition in which underactivity, overactivity or improper activity of an antigen-associated cellular or molecular event is present, and typically results from unusually high (with statistical significance) levels of antigen expression in afflicted cells (e.g., leukemic cells), relative to normal cells. A subject having such a disorder or condition would benefit from treatment with a composition or method of the presently described embodiments. Some conditions associated with antigen overexpression thus may include acute as well as chronic disorders and diseases, such as those pathological conditions that predispose the subject to a particular disorder.

Some examples of conditions associated with antigen overexpression include hyperproliferative disorders, which refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

According to certain embodiments, virtually any type of cancer that is characterized by antigen expression or overexpression may be treated through the use of compositions and methods disclosed herein, including hematological cancers (e.g., leukemia including acute myeloid leukemia (AML), T or B cell lymphomas, myeloma, and others). Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by target antigen overexpression.

Certain methods of treatment or prevention contemplated herein include administering a host cell (which may be autologous, allogeneic or syngeneic) comprising a desired nucleic acid molecule as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, antigen-targeted T-cell composition to a subject, along with an antigen expressing cell composition as an adoptive immunotherapy.

As used herein, administration of a composition or therapy refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., antigen specific recombinant host T cells and antigen expressing cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a recombinant host T cell as described herein is administered to the subject, which may be administered at intervals between administrations of about two to about four weeks, and the subject may be optionally administered an antigen expressing cell as described herein simultaneously, concurrently or subsequent to the administrations of the recombinant (modified) T cells. In further embodiments, a cytokine is administered sequentially, provided that the subject was administered the recombinant host T cell at least three or four times before cytokine administration. In certain embodiments, a cytokine is administered subcutaneously (e.g., IL-2, IL-15, IL-21). In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, a subject being treated has received a non-myeloablative or a myeloablative hematopoietic cell transplant (e.g., autologous, allogeneic), wherein the treatment may be administered at least two to at least three months after the myeloablative or non-myeloablative hematopoietic cell transplant.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a CAR-CTL immune response may be determined by any one of numerous immunological methods described herein and routinely practiced in the art. The level of a CAR-CTL immune response may be determined prior to and following administration of any one of the herein described modified hematopoietic stem cell, immune system cell (e.g., T cell) or any combination thereof. Cytotoxicity assays for determining CTL activity may be performed using any one of several techniques and methods routinely practiced in the art (see, e.g., Henkart et al., "Cytotoxic T-Lymphocytes" in Fundamental Immunology, Paul (ed.) (2003 Lippincott Williams & Wilkins, Philadelphia, Pa.), pages 1127-50, and references cited therein). Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen or Ag-APC used to prime or activate the modified T cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunotherapy) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^6$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

EXAMPLES

Example 1

Characterization of ROR1 CAR-T Cells for Adoptive Transfer Transfer Immunotherapy Human and macaque 4-1BB and CD3ζ signaling molecules are highly conserved (95%), and there is 100% identity of the immunoreceptor tyrosine-based activation motifs of CD3ζ. To ensure the ROR1$^+$ CARs were functional in macaque T cells, T cells were transduced with ROR1 CARs encoding human or macaque 4-1BB and CD3ζ signaling domains, and recognition of ROR1$^+$ target cells was evaluated. To provide a selection marker to purify transduced T cells, a sequence encoding rhesus tCD19 was incorporated in the vector downstream of a T2A ribosomal skip element (Berger et al., *J. Med. Primatol.* 40:88, 2011). The recognition of K562/ROR1 tumor cells by macaque T cells transduced with either a ROR1 CAR containing human 4-1BB/CD3ζ or a ROR1 CAR containing macaque 4-1BB/CD3ζ was equivalent (FIG. 1A). Accordingly, in vivo safety studies using the construct containing the human signaling domains were used to examine the potential clinical translation of this vector.

Figure 1B:
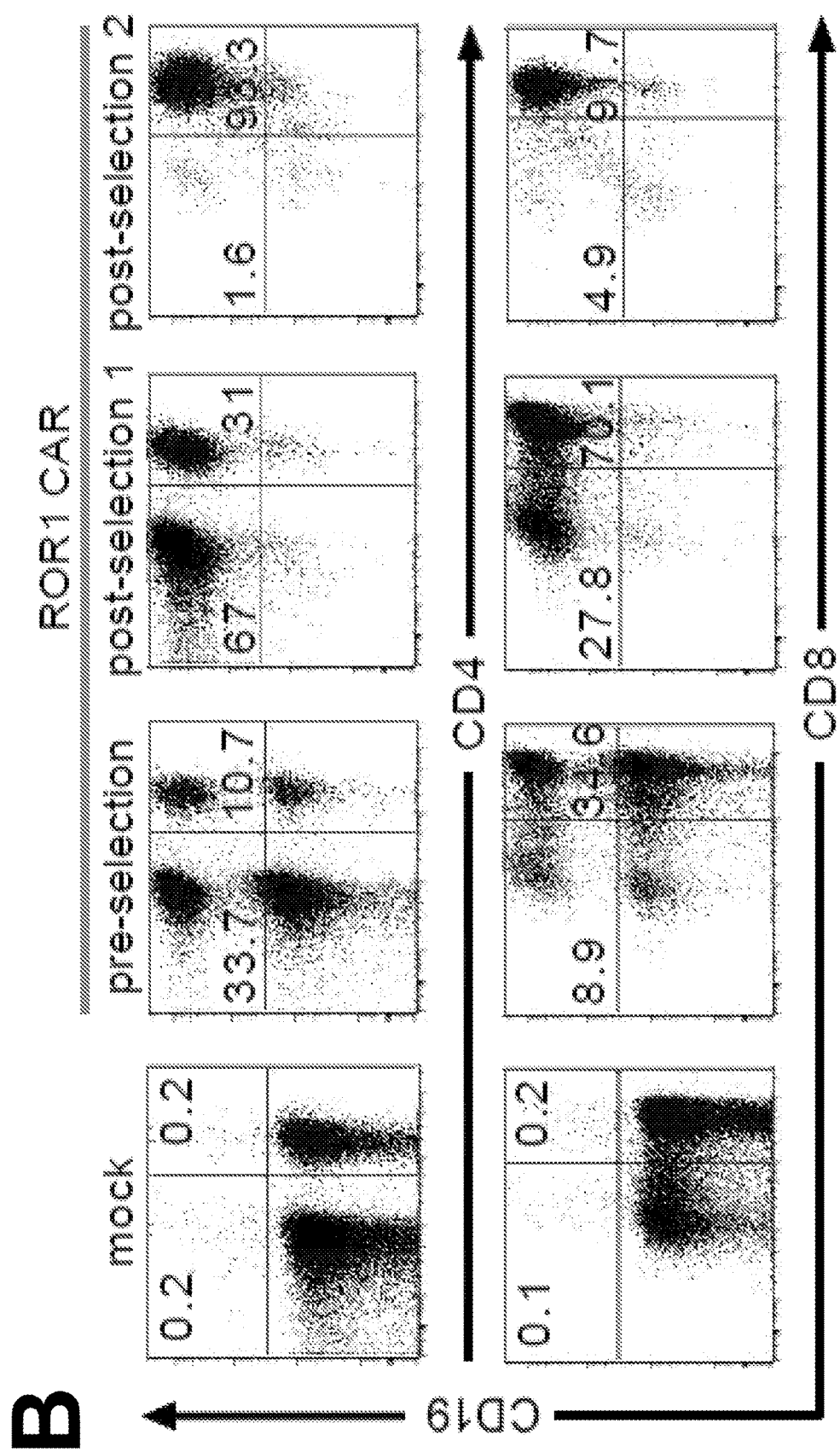

For adoptive transfer experiments, samples of peripheral blood were obtained from three adult rhesus macaques, and PBMC from each animal were stimulated with anti-CD3/CD28 mAbs, and then the T cells were transduced with a ROR1 CAR retroviral vector. The mean transduction efficiency of CD4$^+$ and CD8$^+$ T cells as measured by co-expression of tCD19 was 28.2% (6.6-58.1%) and the transduced cells were enriched to greater than 90% purity by immuno-magnetic selection 4-5 days after transduction (FIG. 1B). Following expansion, a second immuno-magnetic selection was performed to purify CD4$^+$ and CD8$^+$ CAR-T cells, and each subset was expanded separately to allow formulation of an a 1:1 mixture. This ensured a uniform composition of ROR1 CAR-T cells in each adoptive transfer experiment. In addition, autologous CD4$^+$ and CD8$^+$ T cells that were modified to express EGFRt or tCD34 were generated, and prepared as a 1:1 mixture of control transduced CD4$^+$ and CD8$^+$ T cells for co-infusion with ROR1 CAR-T cells.

Figure 1C:
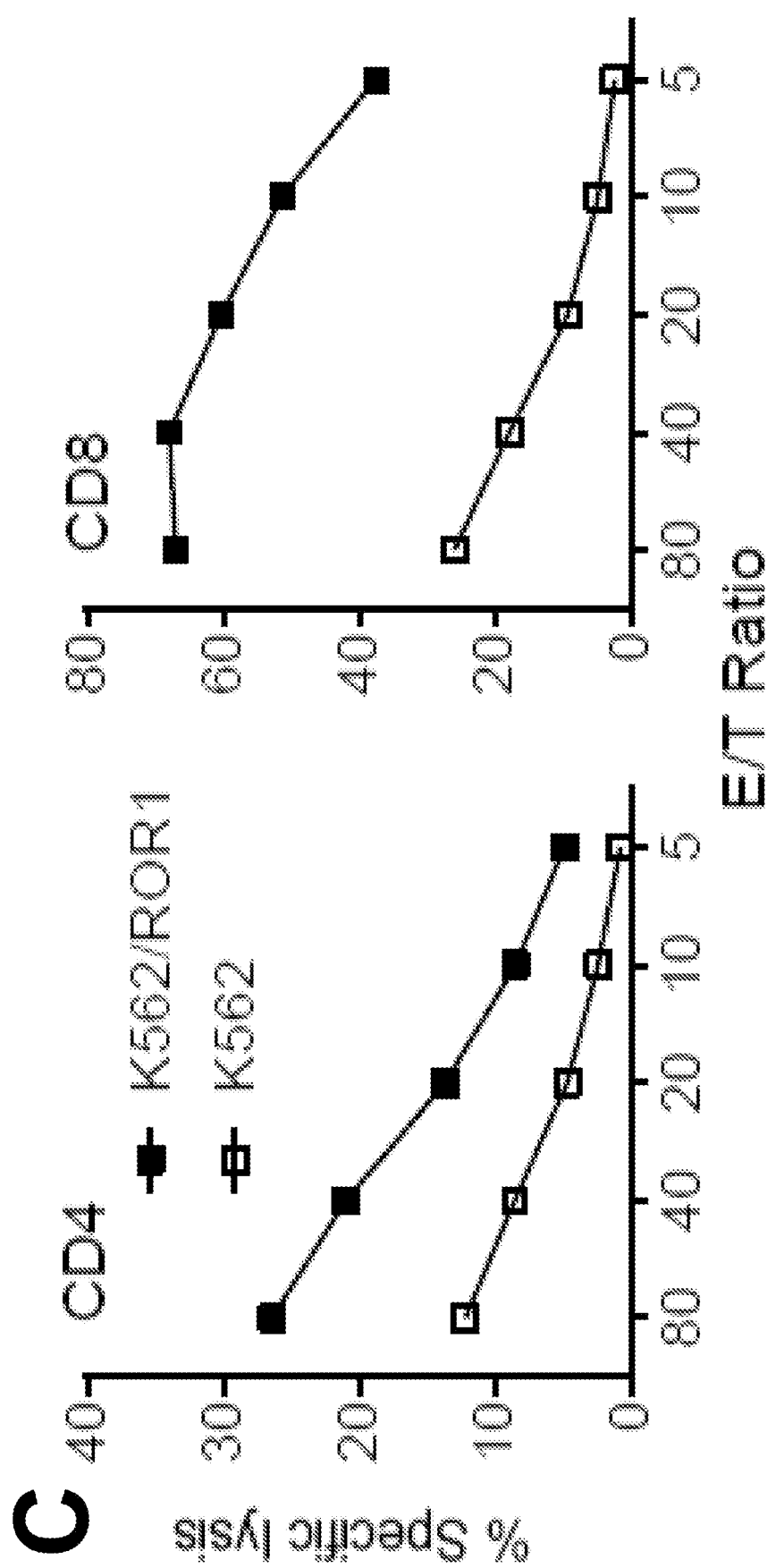

The function of the ROR1 CAR in CD4$^+$ and CD8$^+$ T cells was confirmed by cytotoxicity, proliferation, and cytokine-release assays after co-culture with K562/ROR1 cells. CD8$^+$ ROR1 CAR-T cells lysed K562/ROR1 targets more efficiently than CD4$^+$ ROR1 CAR-T cells (FIG. 1C), and both subsets proliferated and produced cytokines specifically in response to K562/ROR1 cells (FIG. 1D).

Example 2

ROR1 CAR-T Cells are Functional In Vivo

Figures 2A, 2B, 2C:
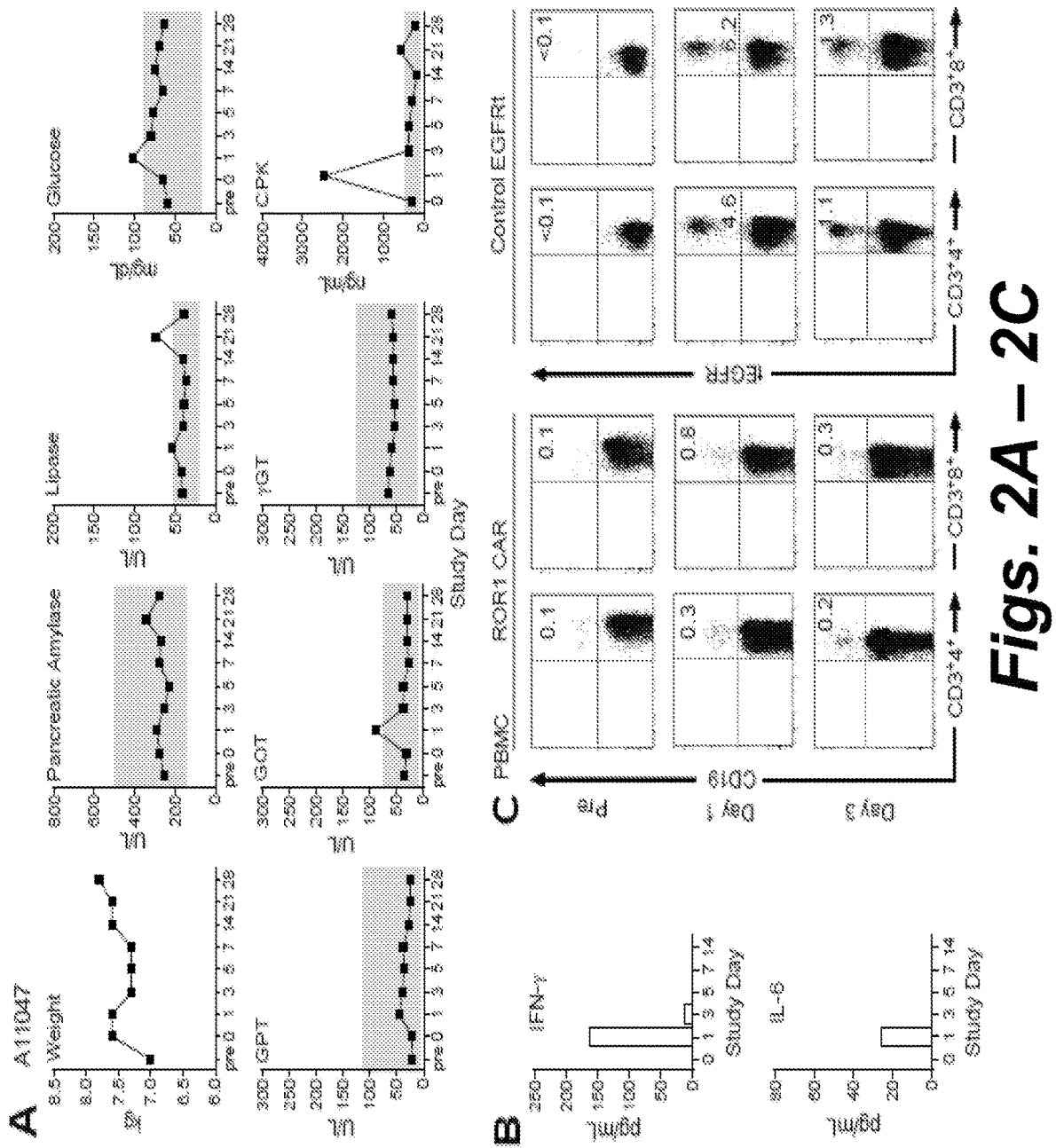
FIGS. 2A-2E show monitoring of toxicity and in vivo persistence of ROR1 CAR-T cells. (A) body weight and serum chemistry before and at the indicated days after the T-cell infusion. The grey shaded area demarks the rhesus macaque specific normal range for each parameter. (B) plasma cytokine levels were measured prior to and post-infusion using a rhesus-specific multiplex cytokine assay. (C) PBMC were obtained before and at the indicated days after the infusion of ROR1 CAR- and control EGFRt$^+$ T cells. The frequency of transferred T cells (%) within the CD3$^+$CD4$^+$ subset and CD3$^+$CD8$^+$ subset was determined by flow cytometry after staining with mAbs specific for CD3, CD4, CD8, and CD19 or for EGFRt. (D) absolute numbers of R12-ROR1 CAR$^+$ and EGFRt$^+$ T cells in the peripheral blood measured by flow cytometry and calculated based on the results of a CBC on the indicated days in an accredited clinical laboratory. (E) DNA was isolated from samples of PBMC obtained on the indicated days and examined by real-time qPCR (TaqMan) for the presence of transgene vector-specific sequences.

To determine if autologous ROR1 CAR-T cells could be transferred safely and to analyze their persistence and migration in vivo, a dose of 1×10$^8$ ROR1 CAR-T cells/kg (CD4:CD8 ratio of 1:1) were administered to a single macaque. This cell dose is less than the dose of CMV-specific T cells administered safely to macaques but equals or exceeds the dose used in clinical trials of CAR-T cell therapy for CD19$^+$ B cell malignancies (Maus et al., *Blood* 123:2625, 2014). Concurrently, the same dose of EGFRt$^+$ T cells was administered to control for cell persistence and migration. The animal was monitored after the T cell infusions for fever, respiratory distress, appetite, diarrhea, and weight loss, and examined pre- and post-infusion blood samples for CBC, serum chemistry, and cytokine levels. No immediate or delayed clinical abnormalities were observed at this cell dose. Body weight, CBC, and serum chemistry remained within normal limits, apart from a transient increase in the muscle-derived creatine phosphokinase (CPK) observed in macaques after intra-muscular (i.m.) ketamine injections for sedation of the animal prior to T-cell infusions (FIG. 2A). Plasma levels of IFN-γ and IL-6 were increased on day 1 after ROR1 CAR-T cells, but returned to normal by day 3 (FIG. 2B). Increases in IFN-γ and IL-6 were not observed after transferring a 5-times higher cell dose of autologous T cells transduced with only a marker gene to a separate animal (data not shown), indicating that the elevated cytokine levels after infusing ROR1 CAR-T cells reflected transient activation of the CAR-T cells in vivo.

Figure 2D:
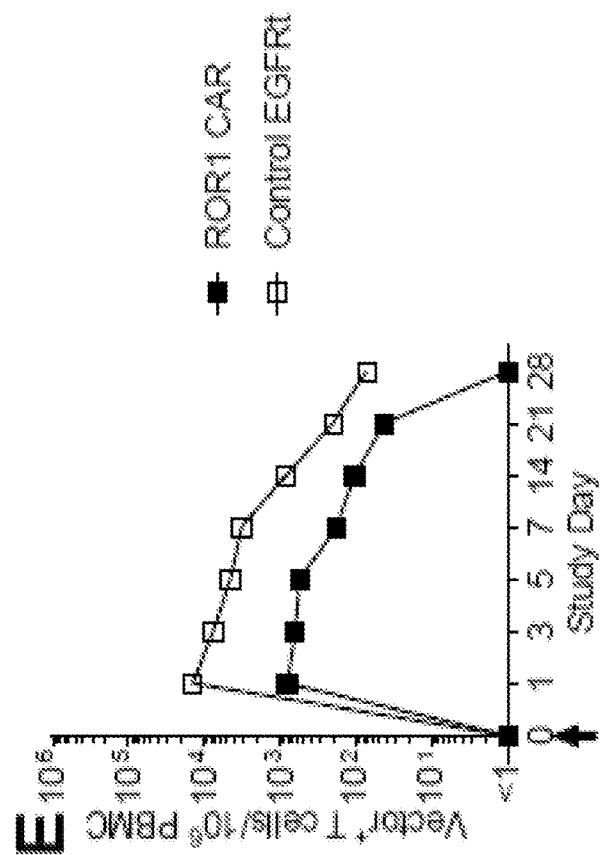
Figure 2E:
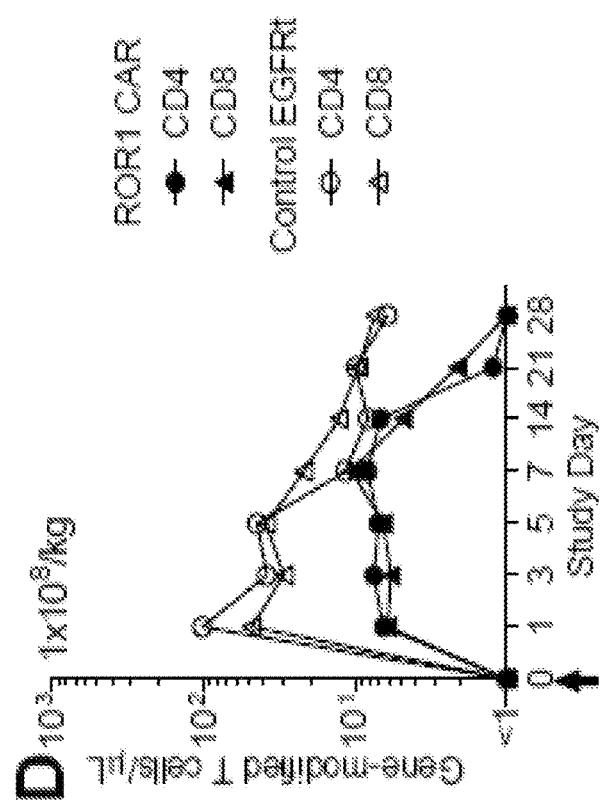

Analysis of the frequency of ROR1 CAR-T cells and control T cells in the blood revealed a difference beginning at the earliest time points after infusion. ROR1 CAR-T cells were detected in the blood one day after the infusion at a frequency of 0.3% of CD4$^+$ and 0.8% of CD8$^+$ T cells (7 cells/μL and 6 cells/μL), and persisted at levels of 4-11 cells/4 over the following 2 weeks. The frequencies of control CD4$^+$ and CD8$^+$ EGFRe T cells were higher on day 1 (6.2% of CD4$^+$ and 4.6% of CD8$^+$ T cells corresponding to 137 cells/4 and 36 cells/4). The EGFRe T cells gradually declined to stable levels of 6-13 cells/4 during the 4-week follow up (FIG. 2C-D). qPCR analysis for transgene-specific sequences confirmed the distinct pattern of in vivo persistence (FIG. 2E).

Figures 3A, 3B, 3C:
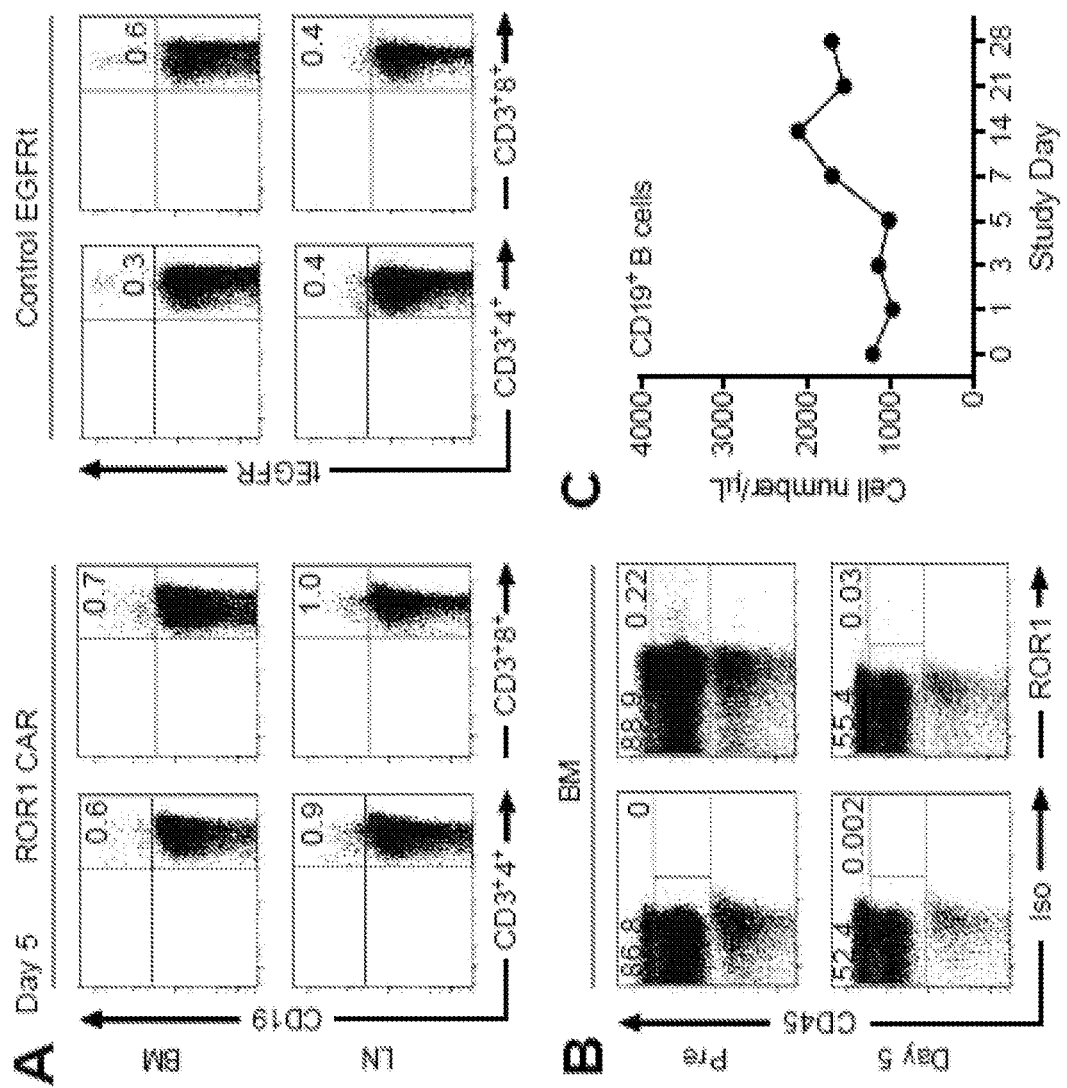
FIGS. 3A-3D show in vivo migration and function of R12-ROR1 CAR-T cells. (A) BM and LN samples obtained prior to and on day 5 after the T-cell infusion were stained with mAbs specific for CD3, CD4, CD8, and CD19 or for EGFRt, and examined by flow cytometry after gating on CD3$^{30}$CD4$^+$ or CD3$^+$CD8$^+$T cells. (B) detection of ROR1$^+$ B-cell precursors in the BM. Samples of BM were obtained before and on day 5 post-infusion and examined by flow cytometry for the presence of a ROR1-expressing CD19$^+$ CD45$^{intermediate}$ B cell subset. (C) absolute number of CD19$^+$ B cells in the peripheral blood samples obtained before and after the T-cell infusion determined by staining with mAbs specific for CD19, CD3, CD4, and CD8 and flow cytometry to detect CD19$^+$CD3$^-$ B cells. Absolute numbers were determined based on the lymphocyte count on a CBC obtained at the same time and determined in an accredited clinical laboratory. (D) CD107A degranulation assay. PBMC were obtained before and at day 7 post-infusion, stimulated ex vivo with K562/ROR1 cells, media, or PMA and Ionomycin, and examined by flow cytometry for expression of CD107A as described in Methods. Cultured ROR1 CAR-T cells served as positive control.

The persistence data indicated that the ROR1 CAR-T cells may be migrating from the blood, perhaps into tissues where ROR1 might be expressed. It was previously shown that a subset of immature B cells in the bone marrow (BM) expresses ROR1 and adoptively transferred macaque T cells migrate to BM and lymph nodes (LNs) (Hudecek et al., *Blood* 116:4532, 2010). Therefore, aliquots of BM and LN samples obtained prior to and on day 5 after infusion was examined for the presence of both ROR1$^+$ B cells and the transferred T cells. EGFRt$^+$ and ROR1 CAR-T cells were present in the day 5 post-infusion BM and LN samples, but the ROR1 CAR-T cells were present at 1.1-2.3-fold higher frequency than the control EGFRt$^+$ T cells (FIG. 3A). A gating strategy to detect the subset of CD19$^+$CD45$^{intermediate}$ B cells was used on BM cell suspensions, which contain the pre-BII-large stage of B-cells that expresses ROR1 in humans (data not shown). ROR1 expression was detected on a subset of CD19$^+$CD45$^{intermediate}$ B cells (8.3%) in the BM obtained prior to the T-cell infusion, and this subset was eliminated in the BM sample obtained on day 5 after transfer of ROR1 CAR-T cells (FIG. 3B). Enumeration of the peripheral blood CD19$^+$ B cells, which are ROR1$^-$, demonstrated that the ROR1 CAR-T cells had no effect on the mature CD19$^+$ B cell pool over the 28 days of the study (FIG. 3C). These results demonstrate that transferred ROR1 CAR-T cells migrated to the BM and recognized and eliminated ROR1$^+$ B-cell precursors, but did not cause organ toxicity or deplete circulating mature B cells.

Figure 3D:
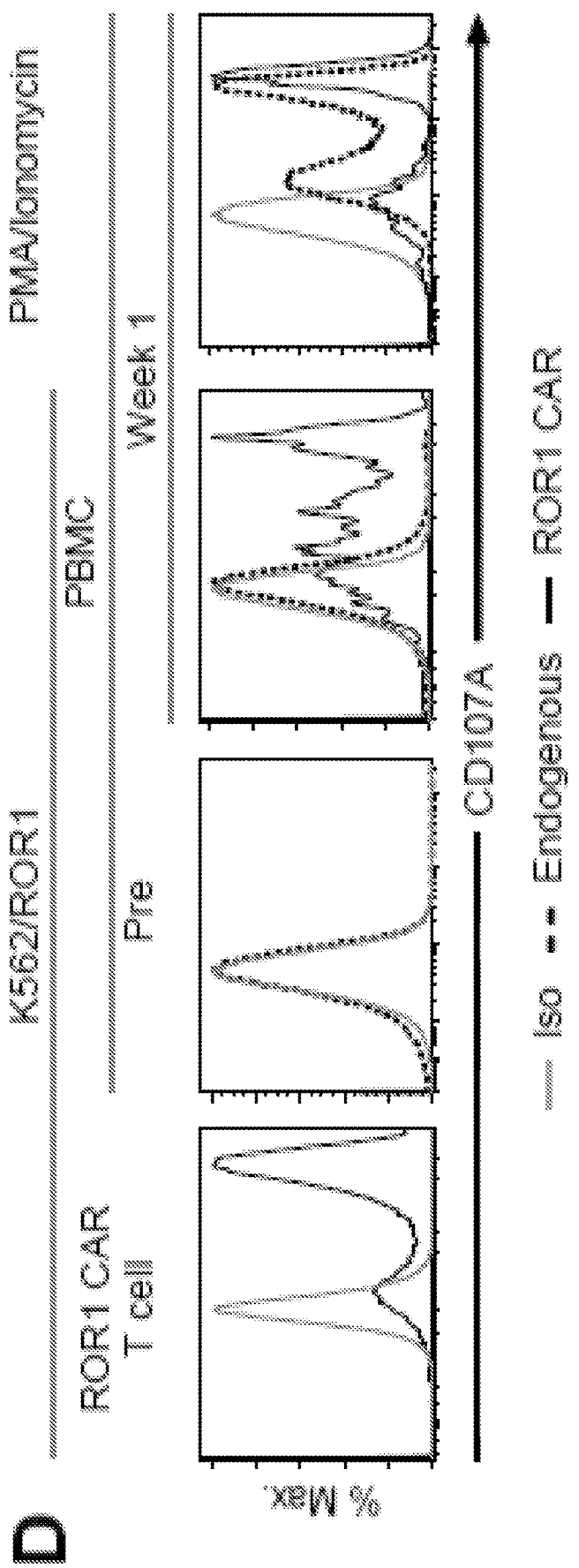

To confirm that the ROR1 CAR-T cells remained functional in vivo, PBMC obtained one week post-infusion were stimulated with K562/ROR1 cells, PMA/Ionomycin, or media alone. Pre-infusion PBMC and ROR1 CAR-T cells served as controls in the assay. After 4 hours of stimulation, the cells were analyzed for expression of CD107A, which is a marker of degranulation after antigen recognition by CD8+ T cells (Chan and Kaur, *J. Immunol. Methods* 325:20, 2007). An increase in CD107A expression was detected in the subset of CD8+ ROR1 CAR-T cells persisting in vivo after stimulation, and this increase was at a similar level as that observed in ROR1 CAR-T cells prior to infusion (FIG. 3D). Thus, transferred ROR1 CAR-T cells that persisted in the blood in vivo remained functional indicating the lack of observed organ toxicity beyond depletion of B-cell precursors was not due to dysfunction of ROR1 CAR-T cells.

Example 3

ROR1 CAR-T Cells Respond to Antigen In Vivo

The infusion of higher CAR-T cell doses may be necessary to treat ROR1+ malignancies and might reveal toxicities to normal tissues, particularly if the CAR-T cells were activated in vivo by recognition of tumor cells expressing high levels of ROR1. During analysis of ROR1-expression on B cells in macaques, it was observed that unlike humans, some animals have a high frequency of mature B cells in the LNs that express ROR1 (data not shown). Two animals with high levels of ROR1+ B cells in LN were selected for analysis of the safety of a higher dose ($5 \times 10^8$/kg) of ROR1 CAR-T cells since experience in the first animal suggested that reduction of ROR1+ B cells provided a surrogate for in vivo function of CAR-T cells. A tCD34 was used as a marker gene in the control T cells in these animals since CD34-enrichment was more efficient than EGFRt-selection, which facilitated obtaining the higher T-cell dose needed for this experiment. To maximize the possibility that activating ROR1 CAR-T cells in vivo might reveal toxicity, an infusion of autologous T cells transfected to express cell-surface tROR1 five days after administration of CAR-T cells was used if no toxicity was observed previously (FIG. 4A).

Figures 4A, 4B:
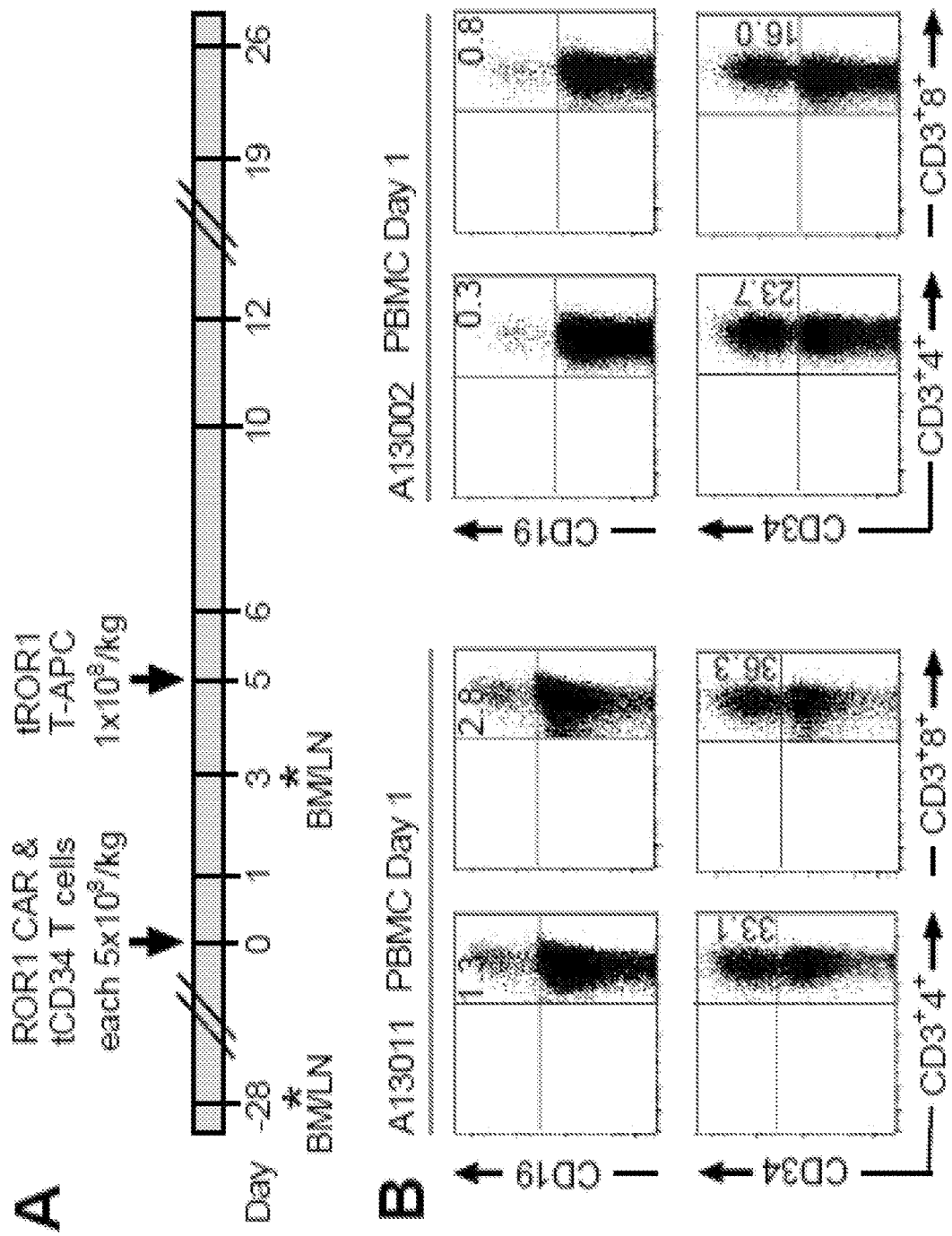
FIGS. 4A-4E show persistence, migration, and safety of ROR1 CAR-T cells given at a high cell dose. (A) schematic overview of the T cell infusions. Autologous ROR1 CAR-T cells were adoptively transferred at a total dose of $5\times10^8$/kg. Control tCD34$^+$ gene-marked T cells were administered at an equivalent dose. Samples of BM and LN were obtained before and on day 3 after the T-cell infusion. (B) flow cytometric analysis of PBMC obtained from macaques A13011 and A13002 before and on day 1 the T-cell infusion. (C) The frequency of transferred T cells (%) within the CD3$^+$CD4$^+$ subset and CD3$^+$CD8$^+$ subset was determined after staining with mAbs specific for CD3, CD4, CD8, and CD19 or for tCD34. C, PBMC, BM, and LN samples were obtained from both macaques on day 3 after the T-cell infusion, stained with mAbs specific for CD3, CD4, CD8, and CD19 or tCD34, and examined by flow cytometry after gating on CD3$^+$CD4$^+$ or CD3$^+$CD8$^+$ cells. The frequency of ROR1 CAR and control tCD34 marked T cells in each subset is shown in the bar graphs for each animal. (D) Frequency of a ROR1 B-cell precursors in the BM before and after ROR1 CAR-T cells. Samples of BM obtained before and 3 days after transfer of ROR1 CAR-T cells were examined by flow cytometry for the presence of ROR1-expressing CD19$^+$CD45$^{intermediate}$ B-cells. Shown are representative stainings of macaque A13011 gated on CD19$^+$ cells. (E) Frequency of ROR1$^+$ B cells in the LN. Samples of LN were obtained before and 3 days after the T-cell infusion, stained with mAbs specific to CD19, CD45, and ROR1 or isotype and examined by flow cytometry for the presence of ROR1$^+$ CD45$^+$ cells within the CD19$^+$ subset. Shown are data from macaque A13011.

The higher dose of ROR1 CAR-T cells were well tolerated and although CD4+ and CD8+ ROR1 CAR-T cells were readily detectable in both animals, a reduced frequency of ROR1 CAR-T cells was again observed as compared to control tCD34 T cells in the blood one day after adoptive transfer (FIG. 4B). The difference in the peak frequency did not reflect unique properties of the marker genes that might influence migration since co-infusion of T cells marked only with tCD19 or tCD34 in a control animal provided equivalently high levels of both populations in vivo (data not shown).

Figures 4C, 4D, 4E:
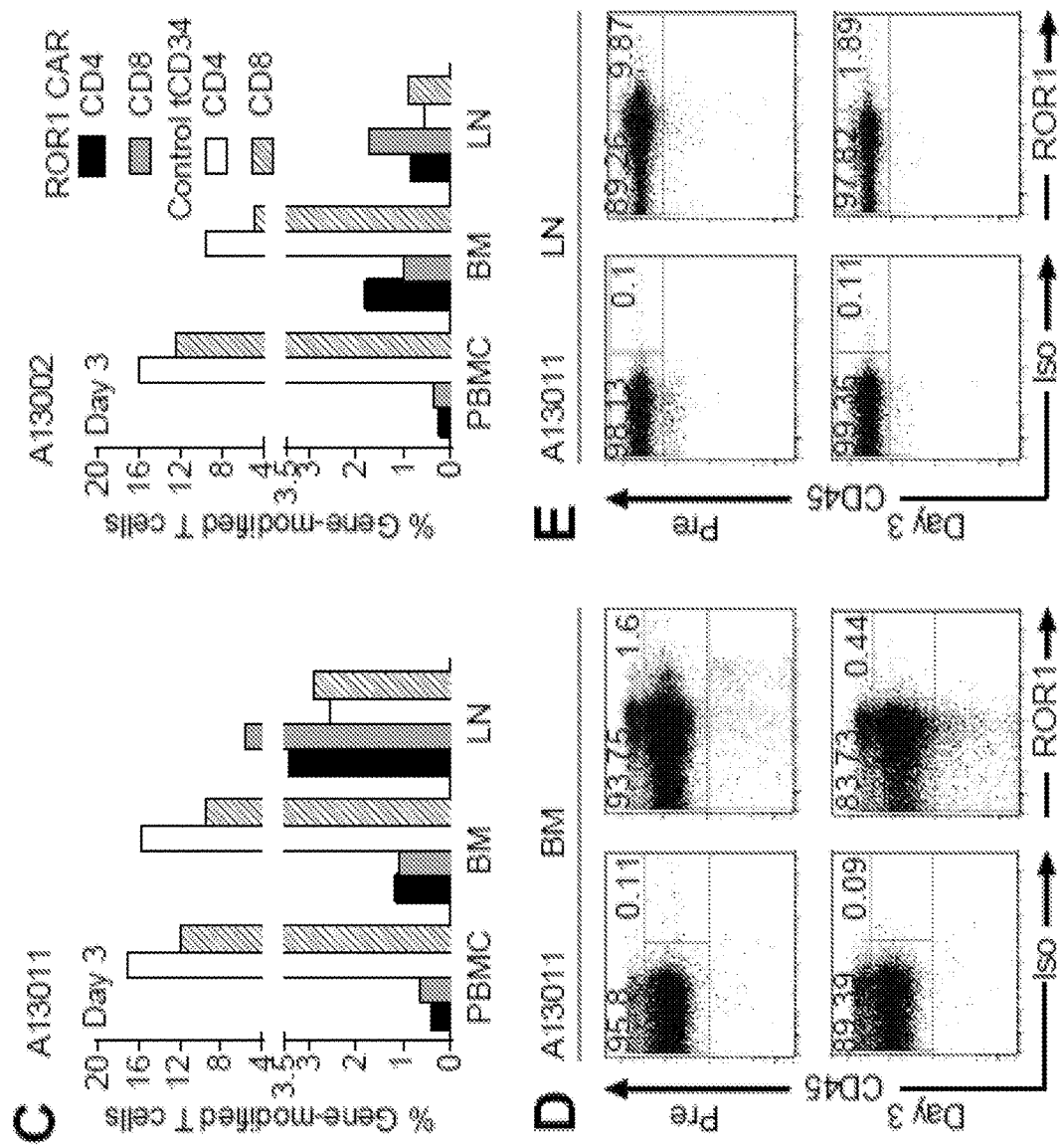

Cell suspensions from PBMC, BM and LNs obtained from each animal at day 3 after infusion were stained for the presence of the transferred T cells. ROR1 CAR-T cells, but not control tCD34+ T cells were present at a higher frequency in the BM than in the PBMC in both animals, and the frequency of ROR1 CAR-T cells in the LN exceeded that of control tCD34+ T cells (FIG. 4C). The accumulation of ROR1 CAR-T cells in BM and LN at day 3 after adoptive transfer coincided with a >65%-80% reduction of ROR1+ B cells compared to the pre-treatment BM and LNs (see FIGS. 4D and 4E). These data are consistent with that observed in the first animal treated with a lower dose of ROR1 CAR-T cells and shows that transferred ROR1 CAR-T cells migrate out of blood and accumulate at sites where ROR1+ B cells reside.

Figures 5A, 5B:
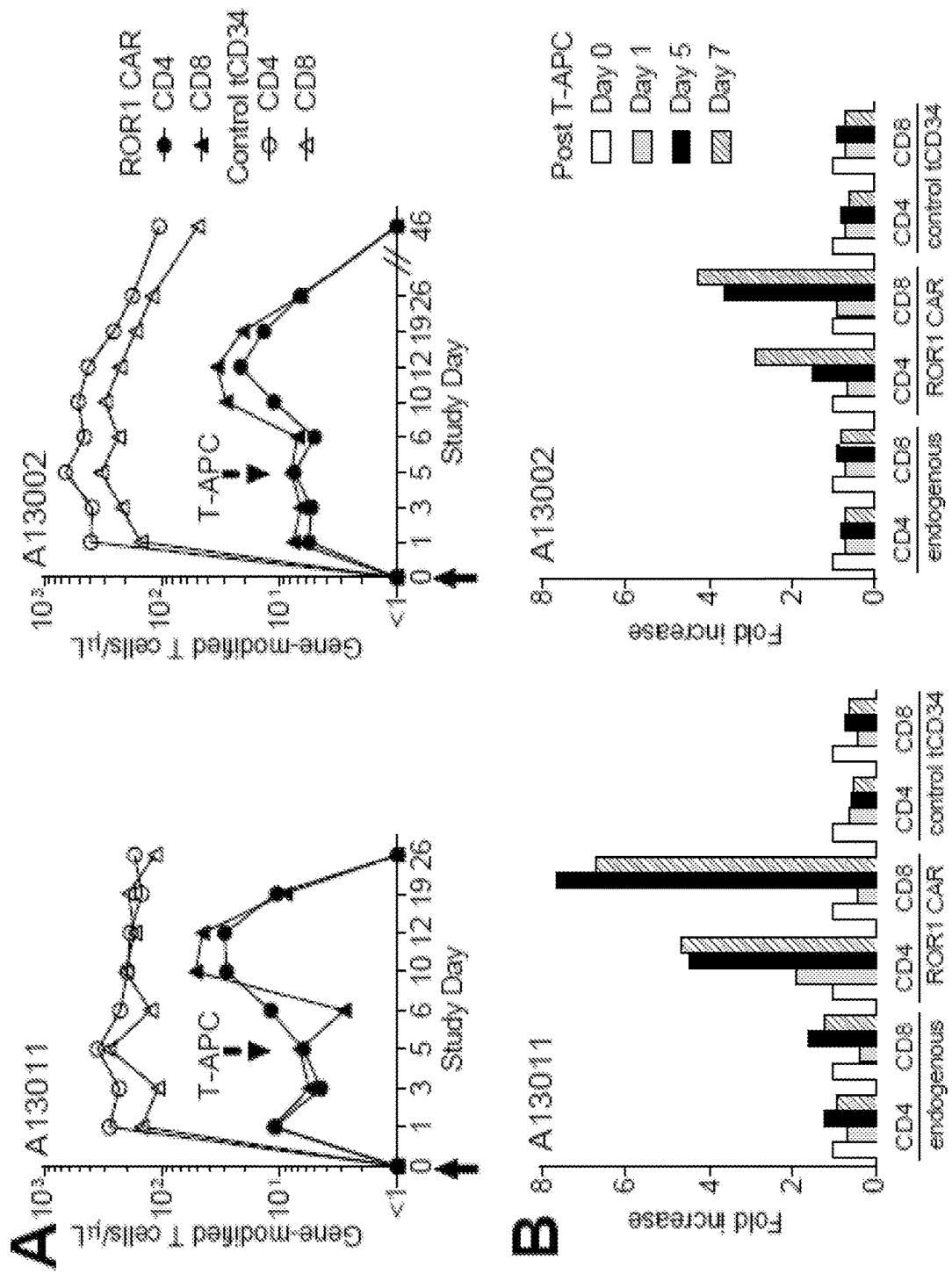
FIGS. 5A-5D show the effect of ROR1+ T cell (T-APC) challenge on transferred ROR1 CAR-T cells in vivo. (A) Samples of PBMC were obtained from A13011 and A13002 at the indicated days and examined by flow cytometry after staining with mAbs specific for CD3, CD4, CD8, and CD19 or for CD34. The CBC was determined in an accredited clinical laboratory. Shown are the absolute numbers of ROR1 CAR$^+$ and tCD34$^+$ T cells in the peripheral blood in the CD3$^+$CD4$^+$ and CD3$^+$CD8$^+$ subset. (B) fold change in the absolute numbers of ROR1 CAR-T cells in the blood after T-APC challenge. The number of CD3$^+$CD8$^+$ T cells and CD19$^+$CD8$^+$ T cells/µL of blood was measured by flow cytometry before and on indicated days after the T-APC administration. The data show the fold-increase over baseline of the absolute numbers of endogenous non-marked CD4$^+$ and CD8$^+$ T cells, R12 ROR1 CAR CD4$^+$ and CD8$^+$ T cells, and tCD34-marked CD4$^+$ and CD8$^+$ T cells after T-APC administration. (C) presence of tROR1$^+$ T cells before and after the T-APC infusion in PBMC samples obtained at days 1, 5, and 7 from an animal (A13011) with persisting ROR1 CAR-T cells. PBMC were stained with anti-CD3 and anti-ROR1 mAbs. (D) presence of tROR1$^+$ T cells before and after the T-APC infusion in PBMC samples obtained at days 1, 5, and 7 from an animal (A12022) without ROR1 CAR-T cells.
Figures 5C, 5D:
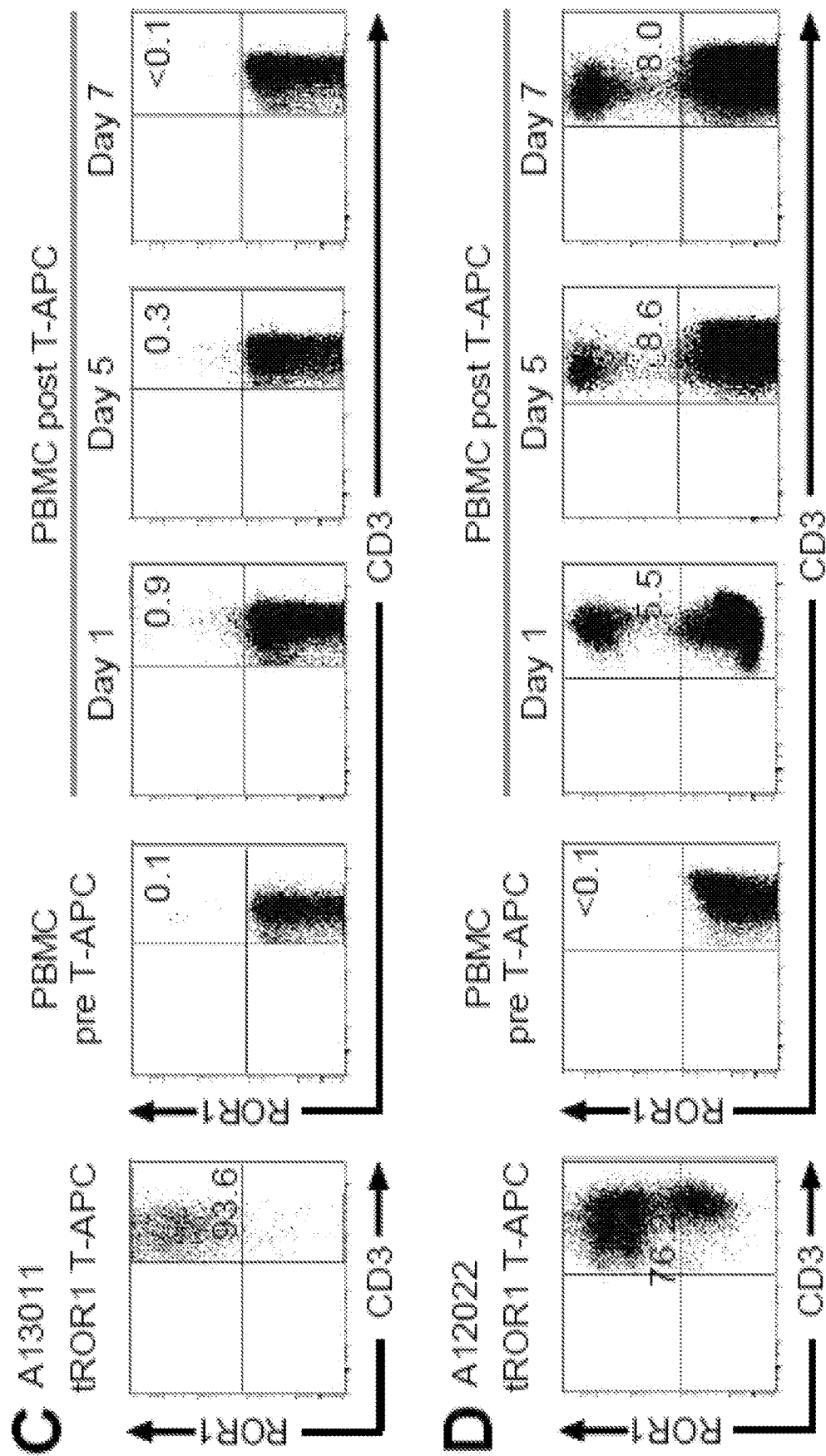

To determine if systemically activating the ROR1 CAR-T cells in vivo might reveal toxicity, autologous T cells that were transduced to express tROR1 (tROR+ T cells) were infused into each animal. In vitro, tROR1-modified T cells were recognized as efficiently as K562/ROR1 cells by autologous ROR1 CAR-T cells (data not shown). The infusion of tROR+ T cells did not cause acute side effects in either animal, and increases in CD4+ and CD8+ ROR1 CAR-T cells was observed to 30 cells/µL and 52 cells/µL (A13011), and to 22 cells/4 and 34 cells/µL (A13002), respectively, over 5-7 days (FIG. 5A). This represented an up to 7.7-fold (A13011) and 4.3-fold (A13002) increase in ROR1 CAR-T cells without substantial changes in numbers of endogenous or tCD34-marked CD4+ and CD8+ T cells (FIG. 5A-B). To determine if the ROR1 CAR-T cells eliminated the tROR+ T cells in vivo, samples of PBMC obtained on day 1, 5, and 7 after T-APC challenge were examined for the presence of circulating tROR+ T cells. In A13011, the tROR+ T cells were present at a frequency of 1.0% of CD8+ T cells one day after transfer and the majority of these cells displayed only low-level ROR1-expression compared to the input tROR1+ T cells (FIG. 5C). Importantly, the ROR1$^{low}$ T cells declined further to a frequency of 0.3% and <0.1% of CD8+ T cells by day 5 and 7, respectively (FIG. 5C). A similar pattern of tROR+ T cell persistence was observed in A13002, with only rare ROR1$^{low}$ T cells persisting in vivo (data not shown). By contrast, the frequencies of tROR1+ T cells in the blood at days 1, 5 and 7 were 5.5%, 8.6%, and 8.0% after infusion of these T cells to an animal without detectable ROR1 CAR-T cells (FIGS. 5C and 5D).

In sum, this demonstrates that recombinantly created "antigen presenting cells" (in this case T cells producing antigen, but other immune system cells and even hematopoietic stem cells may be used as an APC) expressing the same antigen being recognized by a CAR modified T cell can boost or enhance an adoptive transfer immunotherapy.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for improving adoptive cellular immunotherapy, comprising:
   (a) administering to a subject an effective amount of a population of modified human T cells comprising a nucleic acid molecule that encodes an antigen binding protein, wherein the antigen binding protein comprises a hydrophobic portion disposed between an extracellular binding component and an intracellular effector component,
   wherein the binding component is an antibody variable fragment (Fv), a receptor ectodomain, or a ligand, wherein the hydrophobic portion comprises a CD4 transmembrane domain, a CD8 transmembrane domain, a CD28 transmembrane domain, or a CD27 transmembrane domain, and wherein the intracellular effector component comprises an intracellular region of CD3 ε, CD3 δ, CD3ζ, CD25, CD27, CD28, CD79A, CD79B, CD134, CD137, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, ROR2, Ryk, SLAMF1, Slp76, pTα, TCRα, TCRβ, TRIM, Zap70, PTCH2, or any combination thereof; and (b) administering to the subject an effective amount of a population of modified human hematopoietic progenitor cells, modified human immune system cells, or a combination thereof, comprising a nucleic acid molecule that encodes the antigen, wherein the extracellular binding component of the antigen binding protein from the modified human T cells of step (a) is specific for the antigen encoded by the population of modified cells of this step (b), wherein the modified human immune system cells of this step (b) comprise CD4+ T cells, CD8+ T cells, CD4- CD8- double negative T cells, γδ T cells, natural killer cells, or any combination thereof;

thereby boosting, augmenting or enhancing the efficacy of the adoptive cellular immunotherapy.

2. A method for treating a disease in a subject, comprising:
(a) administering to a subject an effective amount of a population of modified human T cells comprising a nucleic acid molecule that encodes an antigen binding protein, wherein the antigen binding protein comprises a hydrophobic portion disposed between an extracellular binding component and an intracellular effector component,
wherein the binding component is an antibody variable fragment (Fv), a receptor ectodomain, or a ligand,
wherein the hydrophobic portion comprises a CD4 transmembrane domain, a CD8 transmembrane domain, a CD28 transmembrane domain, or a CD27 transmembrane domain,
and wherein the intracellular effector component comprises an intracellular region of CD3 ε, CD3 δ, CD3ζ, CD25, CD27, CD28, CD79A, CD79B, CD134, CD137, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, ROR2, Ryk, SLAMF1, Slp76, pTα, TCRα, TCRβ, TRIM, Zap70, PTCH2, or any combination thereof;
(b) administering to the subject an effective amount of a population of modified human hematopoietic progenitor cells, modified human immune system cells or a combination thereof comprising a nucleic acid molecule that encodes the antigen, wherein the extracellular binding component of the antigen binding protein from the modified human T cells of step (a) is specific for the antigen encoded by the population of modified cells of this step (b),
wherein the modified human immune system cells of this step (b) comprise CD4+ T cells, CD8+ T cells, CD4- CD8- double negative T cells, γδ T cells, natural killer cells, or any combination thereof; and
(c) optionally repeating step (a), step (b) or both steps (a) and (b);
thereby treating the disease by adoptive cellular immunotherapy.

3. The method according to claim 2, wherein the disease is a viral disease, a bacterial disease, a cancer, an inflammatory disease, an immune disease, or an aging-associated disease.

4. The method according to claim 2, wherein the disease is a hyperproliferative disease.

5. The method according to claim 4, wherein the hyperproliferative disorder is:
(a) a hematological malignancy selected from acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), or multiple myeloma (MM); or
(b) a solid cancer selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

6. The method according to claim 1, wherein the binding component is an antibody variable fragment (Fv).

7. The method according to claim 6, wherein the binding component is a scFv comprising a variable region linker, wherein the variable region linker comprises a $(Gly_xSer_y)_n$, wherein x and y are independently an integer from 1 to 5, and n is an integer from 1 to 10.

8. The method according to claim 1, wherein the intracellular effector component comprises an intracellular region of CD3ζ, CD137, or both.

9. The method according to claim 1, wherein the binding component is specific for α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFEβ, LRP5, MAGE, mesothelin, MUC1, NY-ESO-1, a cancer-specific neoantigen, OSMRβ, PD1, PD-L1, PD-L2, PSMA, PTCH1, RANK, Robo1, ROR1, TERT, TGFBR2, TGFBR1, TLR7, TLR9, TNFRSF4, TNFR1, TNFR2, tyrosinase, TWEAK-R, or WT-1.

10. The method according to claim 1, wherein the antigen binding protein is a chimeric antigen receptor.

11. The method according to claim 1, wherein the immune system cell is a CD4+ T cell, a CD8+ T cell, a CD4- CD8- double negative T cell, a γδ T cell, or any combination thereof.

12. The method according to claim 1, wherein the first population of modified T cells consists essentially of CD4+ T cells, CD8+ T cells, or both CD4+ and CD8+ T cells.

13. The method according to claim 1, wherein the second population of modified cells comprises modified human hematopoietic progenitor cells or modified human immune system cells, wherein the modified immune system cells consist essentially of CD4+ T cells, a CD8+ T cells, or both CD4+ and CD8+ T cells.

14. The method according to claim 1, wherein the cells are recombinantly modified ex vivo using a viral vector.

15. The method according to claim 14, wherein the viral vector is a lentiviral vector or a γ-retroviral vector.

16. The method according to claim 1, wherein the population of modified cells of step (a) and of the population of modified cells of step (b) is allogeneic, syngeneic, or autologous to the subject.

17. The method according to claim 1, wherein the extracellular binding component of the antigen binding protein from the modified human T cells is directed against a cell overexpressing the antigen.

18. The method according to claim 1, wherein the method comprises administering to the subject a plurality of doses of the modified T cells from step (a), a plurality of doses of modified cells from step (b), or a combination thereof.

19. The method according to claim 18, wherein the plurality of doses of modified T cells from step (a) are administered at intervals between administrations of about one week to about four weeks.

20. The method according to claim 1, wherein the modified T cells from step (a) are administered concurrently or sequentially with the modified cells from step (b).

21. The method according to claim 20, wherein the initial dose of modified cells from step (b) are administered from about 1 day to about 28 days after administering the modified T cells from step (a).

22. The method according to claim 20, wherein the modified cells from step (b) are modified hematopoietic progenitor cells.

23. The method according to claim 20, wherein the modified cells from step (b) are modified T cells.

24. The method according to claim 1, wherein the modified T cells from step (a) are administered to the subject at a dose of about $10^6$ cells/m$^2$ to about $10^{11}$ cells/m$^2$ and the modified T cells from step (b) are administered to the subject at a dose of about $10^6$ cells/m$^2$ to about $10^{11}$ cells/m2.

25. An adoptive cellular immunotherapy composition, comprising a population of modified human hematopoietic progenitor cells, modified human immune system cells or a combination thereof, wherein a first population of modified cells are T cells comprising a nucleic acid molecule that encodes an antigen binding protein, and a second population of modified cells comprising a nucleic acid molecule that encodes the antigen,
  wherein the antigen binding protein comprises a hydrophobic portion disposed between an extracellular binding component and an intracellular effector component,
  wherein the binding component is an antibody variable fragment (Fv), a receptor ectodomain, or a ligand,
  wherein the hydrophobic portion comprises a CD4 transmembrane domain, a CD8 transmembrane domain, a CD28 transmembrane domain, or a CD27 transmembrane domain,
  wherein the intracellular effector component comprises an intracellular region of CD3ε, CD3 δ, CD3 ζ, CD25, CD27, CD28, CD79A, CD79B, CD134, CD137, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, ROR2, Ryk, SLAMF1, Slp76, pTα, TCRα, TCRβ, TRIM, Zap70, PTCH2, or any combination thereof,
  wherein the second population of modified cells comprise CD4+ T cells, CD8+ T cells, CD4-CD8– double negative T cells, γδ T cells, natural killer cells, or any combination thereof, and
  wherein the extracellular binding component is specific for the antigen encoded by the second population of modified cells.

26. The adoptive cellular immunotherapy composition of claim 25, wherein:
  (i) the binding component of the antigen-binding protein is a scFv;
  (ii) the intracellular effector component of the antigen-binding protein comprises an intracellular region of CD3ζ, CD137, or both; and
  (iii) the second population of modified cells comprises CD4+ T cells, CD8+ T cells, CD4-CD8– double negative T cells, γδ T cells, or any combination thereof.

27. The method of claim 1, wherein the modification of the human hematopoietic progenitor cells, the human immune system cells, or the combination thereof, of step (b) consists essentially of the nucleic acid that encodes the antigen.

28. The method of claim 2, wherein the modification of the human hematopoietic progenitor cells, the human immune system cells, or the combination thereof, of step (b) consists essentially of the nucleic acid that encodes the antigen.

29. The adoptive cellular immunotherapy composition of claim 25, wherein the modification of the second population of cells consists essentially of the nucleic acid that encodes the antigen.

30. The method of claim 1, wherein the administering in step (a), in step (b), or both, comprises intravenous administration of the cells.

31. The method of claim 2, wherein the administering in step (a), in step (b), or both, comprises intravenous administration of the cells.

* * * * *